(12) United States Patent
Binner et al.

(10) Patent No.: US 11,247,226 B2
(45) Date of Patent: Feb. 15, 2022

(54) PROCESS FOR FORMING A MULTILAYERED SHAPED FILM PRODUCT

(71) Applicant: Johnson & Johnson Consumer Inc., Skillman, NJ (US)

(72) Inventors: Curt Binner, Furlong, PA (US); Kenneth A. Pelley, Hopewell, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 70 days.

(21) Appl. No.: 16/366,533

(22) Filed: Mar. 27, 2019

(65) Prior Publication Data

US 2019/0217333 A1    Jul. 18, 2019

Related U.S. Application Data

(62) Division of application No. 14/580,977, filed on Dec. 23, 2014, now abandoned.

(Continued)

(51) Int. Cl.
| | |
|---|---|
| *B32B 3/00* | (2006.01) |
| *B05D 1/32* | (2006.01) |
| *B05D 1/28* | (2006.01) |
| *C09D 105/00* | (2006.01) |
| *A61K 9/70* | (2006.01) |

(52) U.S. Cl.
CPC ............ *B05D 1/322* (2013.01); *A61K 9/7007* (2013.01); *B05D 1/28* (2013.01); *C09D 105/00* (2013.01); *Y10T 428/24851* (2015.01)

(58) Field of Classification Search
CPC .................. B05D 1/322; A61K 9/7007; Y10T 428/42802
See application file for complete search history.

(56) References Cited

U.S. PATENT DOCUMENTS

| | | | |
|---|---|---|---|
| 2,122,451 | A | 7/1938 | Cassimatis |
| 2,267,787 | A | 12/1941 | Ciavola |
| | (Continued) | | |

FOREIGN PATENT DOCUMENTS

| | | |
|---|---|---|
| CA | 2250025 C | 10/2006 |
| CN | 1148535 A | 4/1997 |
| | (Continued) | |

OTHER PUBLICATIONS

U.S. Appl. No. 14/580,974, filed Dec. 23, 2014, 2015-0182991, Jul. 20, 2015, Abandoned.

(Continued)

*Primary Examiner* — Elizabeth E Mulvaney

(57) ABSTRACT

A process capable of commercial scale manufacturing of inexpensive, multilayered shaped film product, without the waste of die-cutting and which products are capable of use independent of a supporting structure on which they are formed, includes placing a first mask over a substrate; delivering a first film-forming composition through the first mask to form a first raw shape on the substrate; removing the first mask; placing a second mask over the first raw shape; delivering a second film-forming composition through the second mask to form a second raw shape on the first raw shape; removing the second mask; and solidifying the first and second raw shapes to provide the shaped film product disposed on the substrate.

7 Claims, 16 Drawing Sheets

Related U.S. Application Data

(60) Provisional application No. 61/922,296, filed on Dec. 31, 2013.

(56) References Cited

U.S. PATENT DOCUMENTS

| | | |
|---|---|---|
| 2,511,511 A | 6/1950 | Murphy |
| 2,523,670 A | 9/1950 | Schueler |
| 2,852,252 A | 9/1958 | Sperry |
| 3,198,109 A | 8/1965 | Dwyer et al. |
| 3,421,455 A | 1/1969 | Werner |
| 3,476,045 A | 11/1969 | Lusher |
| 3,503,345 A | 3/1970 | Abrams |
| 3,658,977 A | 4/1972 | Baker |
| 3,890,896 A | 6/1975 | Zimmer |
| 3,994,220 A | 11/1976 | Vertegaal |
| 4,023,487 A | 5/1977 | Mitter |
| 4,050,409 A | 9/1977 | Duchenaud et al. |
| 4,068,994 A | 1/1978 | Cadwallader et al. |
| 4,219,596 A | 8/1980 | Takemoto et al. |
| 4,379,185 A | 4/1983 | Smith et al. |
| 4,391,853 A | 7/1983 | Pointon |
| 4,419,168 A | 12/1983 | Paul |
| 4,466,431 A | 8/1984 | Tharrat et al. |
| 4,537,647 A | 8/1985 | Foster |
| 4,604,966 A | 8/1986 | Kohn |
| 4,665,723 A | 5/1987 | Zimmer |
| 4,699,792 A | 10/1987 | Asmussen et al. |
| 4,930,413 A | 6/1990 | Jaffa |
| 4,990,339 A | 2/1991 | Scholl et al. |
| 5,017,394 A | 5/1991 | Macpherson et al. |
| 5,128,124 A * | 7/1992 | Fankhauser .......... A61K 31/565 424/449 |
| 5,251,566 A | 10/1993 | Kobayashi et al. |
| 5,264,269 A | 11/1993 | Kakiuchi et al. |
| 5,393,529 A | 2/1995 | Hoffmann et al. |
| 5,474,802 A | 12/1995 | Shimoda et al. |
| 5,553,536 A | 9/1996 | Van Os |
| 5,553,539 A | 9/1996 | Hasegawa |
| 5,572,928 A | 11/1996 | Negishi |
| 5,578,151 A | 11/1996 | Andris et al. |
| 5,622,108 A | 4/1997 | Benedetto et al. |
| 5,700,478 A | 12/1997 | Biegajski et al. |
| 5,746,127 A | 5/1998 | Fischbeck et al. |
| 5,780,142 A | 7/1998 | Kume et al. |
| 5,780,418 A | 7/1998 | Niinaka et al. |
| 5,800,832 A | 9/1998 | Tapolsky et al. |
| 5,814,260 A | 9/1998 | Arai |
| 5,914,118 A | 6/1999 | Yamamura et al. |
| 5,925,414 A | 7/1999 | Buechele et al. |
| 5,948,430 A | 9/1999 | Zerbe et al. |
| 6,092,464 A | 7/2000 | Meola et al. |
| 6,132,510 A | 10/2000 | Buechele et al. |
| 6,159,498 A | 12/2000 | Tapolsky et al. |
| 6,199,479 B1 | 3/2001 | Isozaki et al. |
| 6,238,741 B1 | 5/2001 | Blazick et al. |
| 6,395,087 B1 | 5/2002 | Jairazbhoy et al. |
| 6,429,261 B1 | 8/2002 | Lang et al. |
| 6,444,214 B1 | 9/2002 | Cole et al. |
| 6,495,080 B1 | 12/2002 | Tsai et al. |
| 6,537,663 B1 | 3/2003 | Chang et al. |
| 6,548,592 B1 | 4/2003 | Lang et al. |
| 6,565,839 B2 | 5/2003 | de la Poterie et al. |
| 6,576,575 B1 | 6/2003 | Griesbach, III et al. |
| 6,592,887 B2 | 7/2003 | Zerbe et al. |
| 6,595,129 B2 | 7/2003 | Mori |
| 6,656,274 B2 | 12/2003 | Claassen et al. |
| 6,659,004 B2 | 12/2003 | Tagami |
| 6,712,906 B2 | 3/2004 | Estelle et al. |
| 6,722,275 B2 | 4/2004 | Coleman et al. |
| 6,800,295 B2 | 10/2004 | Fox |
| 6,946,501 B2 | 9/2005 | Kochvar et al. |
| 6,989,327 B2 | 1/2006 | Sharma et al. |
| 7,285,520 B2 | 10/2007 | Krzysik et al. |
| 7,332,230 B1 | 2/2008 | Krumme |
| 7,378,360 B2 | 5/2008 | Clark et al. |
| 7,387,787 B2 | 6/2008 | Fox |
| 7,579,019 B2 | 8/2009 | Tapolsky et al. |
| 7,612,048 B2 | 11/2009 | Pinna et al. |
| 7,803,430 B2 | 9/2010 | Krumme |
| 8,042,463 B2 | 10/2011 | Sato |
| 8,268,764 B2 | 9/2012 | Glenn, Jr. et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,354,393 B2 | 1/2013 | Maruyama |
| 8,415,287 B2 | 4/2013 | Glenn, Jr. et al. |
| 8,741,194 B1 | 6/2014 | Ederer et al. |
| 2001/0004152 A1 | 6/2001 | Treleaven et al. |
| 2002/0068251 A1 | 6/2002 | Steck |
| 2002/0098994 A1 | 7/2002 | Zafar |
| 2002/0127254 A1 | 9/2002 | Fotinos et al. |
| 2002/0160062 A1 | 10/2002 | Liu et al. |
| 2002/0192287 A1 | 12/2002 | Mooney et al. |
| 2003/0175333 A1 | 9/2003 | Shefer et al. |
| 2003/0209485 A1 | 11/2003 | Kools |
| 2003/0211136 A1 | 11/2003 | Kulkarni et al. |
| 2003/0235606 A1 | 12/2003 | Nussen |
| 2003/0235630 A1 | 12/2003 | Nussen |
| 2004/0137040 A1 | 7/2004 | Nogami |
| 2004/0180077 A1 | 9/2004 | Riker |
| 2005/0145832 A1 | 7/2005 | Wessling et al. |
| 2005/0208110 A1 | 9/2005 | Singh et al. |
| 2006/0002987 A1 | 1/2006 | Bevacqua et al. |
| 2007/0298076 A1 | 12/2007 | Biegajski |
| 2008/0057087 A1 | 3/2008 | Krumme |
| 2008/0102103 A1 | 5/2008 | Bevacqua et al. |
| 2008/0282914 A1 | 11/2008 | Black et al. |
| 2010/0053577 A1 | 3/2010 | Lee et al. |
| 2011/0020450 A1* | 1/2011 | Wright, IV ............. A61P 25/18 424/484 |
| 2011/0146509 A1 | 6/2011 | Welygan et al. |
| 2012/0094004 A1* | 4/2012 | Stopek ................... A61L 31/16 427/2.1 |
| 2012/0100202 A1* | 4/2012 | Bogue ................... B29C 41/28 424/443 |
| 2012/0141698 A1 | 6/2012 | Oleary et al. |
| 2012/0201964 A1 | 8/2012 | Zhou et al. |
| 2013/0092721 A1 | 4/2013 | Trelford et al. |
| 2014/0155845 A1* | 6/2014 | Aigle ..................... A61K 9/703 604/307 |
| 2015/0182990 A1 | 7/2015 | Binner et al. |
| 2015/0182991 A1 | 7/2015 | Binner et al. |
| 2015/0182992 A1 | 7/2015 | Binner et al. |
| 2015/0182993 A1 | 7/2015 | Binner et al. |
| 2017/0354990 A1 | 12/2017 | Binner et al. |
| 2017/0368568 A1 | 12/2017 | Binner et al. |

FOREIGN PATENT DOCUMENTS

| | | |
|---|---|---|
| CN | 201240095 Y | 5/2009 |
| CN | 103476565 A | 12/2013 |
| DE | 3423328 A1 | 1/1986 |
| EP | 2472331 A1 | 4/1995 |
| EP | 0781546 A | 7/1997 |
| EP | 1110541 A1 | 6/2001 |
| EP | 1149572 A1 | 10/2001 |
| FR | 2710869 A1 | 4/1995 |
| JP | 49135714 A | 12/1974 |
| JP | S57170732 A | 10/1982 |
| JP | S59184819 U1 | 12/1984 |
| JP | 63171565 A | 7/1988 |
| JP | H03122821 U1 | 12/1991 |
| JP | H10156849 A | 6/1998 |
| JP | 2003126761 A | 5/2003 |
| JP | 2007160643 A | 6/2007 |
| JP | 2011012010 A | 1/2011 |
| JP | 201286015 | 5/2012 |
| JP | 2012186015 | 9/2012 |
| JP | 2013075446 A | 4/2013 |
| JP | 2013188872 | 9/2013 |
| JP | 2013540161 A | 10/2013 |
| JP | 2015086015 A | 5/2015 |

(56) References Cited

FOREIGN PATENT DOCUMENTS

| OA | 2974 A | 12/1970 |
|---|---|---|
| WO | WO1998/017251 A | 4/1998 |
| WO | WO2001/034121 A | 5/2001 |
| WO | WO2005/009386 A | 2/2005 |
| WO | WO2009/084234 A | 7/2009 |
| WO | WO2010/146998 A | 12/2010 |
| WO | WO2012/054810 A | 4/2012 |
| WO | WO2012/104834 A | 8/2012 |
| WO | WO2014/116770 A | 7/2014 |

OTHER PUBLICATIONS

U.S. Appl. No. 61/922,287, Expired.
U.S. Appl. No. 16/366,533, filed Mar. 27, 2019, 2019-0217333, Jul. 18, 2019, Pending.
U.S. Appl. No. 14/580,977, filed Dec. 23, 2014, Jul. 2, 2015, Abandoned.
U.S. Appl. No. 61/922,296, Dec. 31, 2013, Expired.
U.S. Appl. No. 16/584,146, filed Sep. 26, 2019, Pending.
U.S. Appl. No. 14/581,010, filed Dec. 23, 2014, 2015-0182993, Jul. 2, 2015, Pending.
U.S. Appl. No. 61/922,306, Dec. 31, 2013, Expired.
U.S. Appl. No. 15/688,217, filed Aug. 28, 2017, 2017-0368568, Dec. 28, 2017, Abandoned.
U.S. Appl. No. 15/688,411, filed Aug. 28, 2017, 2017-0354990, Dec. 14, 2017, 10016784, Jul. 10, 2018, Grant.
U.S. Appl. No. 14/581,057, filed Dec. 23, 2014, 2015-0182990, Jul. 2, 2015, 9839939, Dec. 12, 2017, Grant.
U.S. Appl. No. 61/922,318, filed Dec. 31, 2013, Expired.
International search report dated Apr. 28, 2015, for international application PCT/US2014/072101.
Ebara, "Techniques of Wallpaper manufactured by Rotary Screen Printing", Journal of Printing Science and Technology, Japan, 2001, 38(1):13-17.
Kapur et al., "Predicting the Behavior of Screen Printing", IEEE Transactions on Components, Packaging and Manufacturing Technology, vol. 3, No. 3 (Mar. 2013), pp. 508-515.
Willfahrt et al., "Optimising Stencil Thickness and Ink Film Deposit", (2011), International Circular of Graphic Education and Research.
Chang et al., "Pharmaceutics", China Medical Science and Technology Press, 2008, pp. 265-266.

* cited by examiner

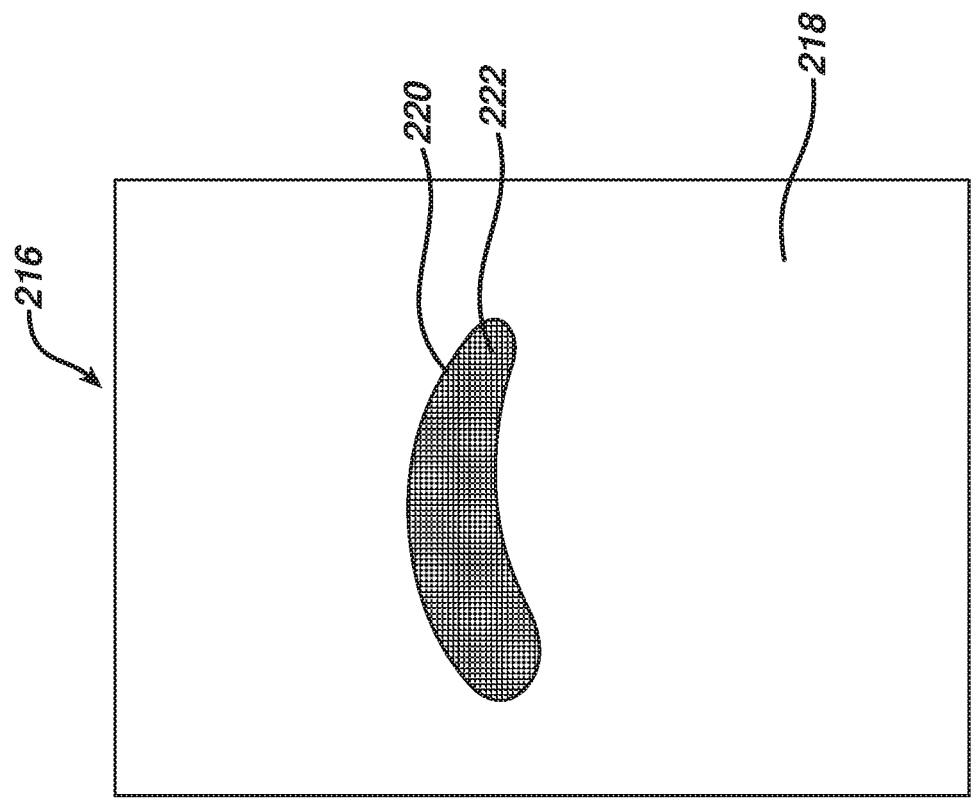
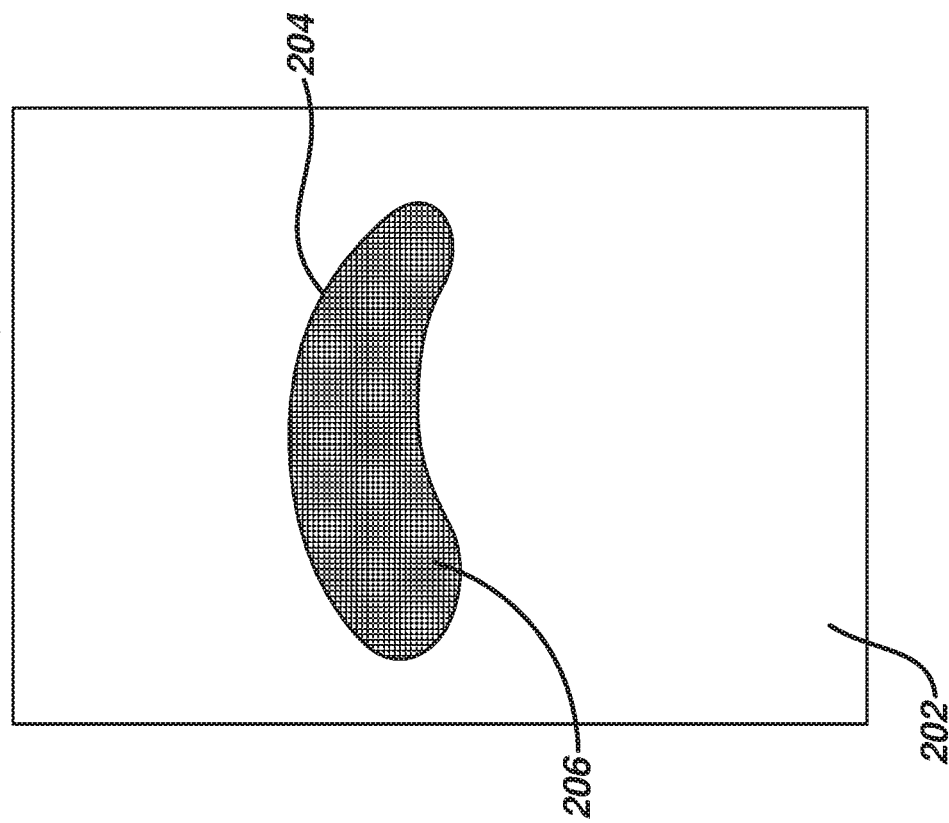

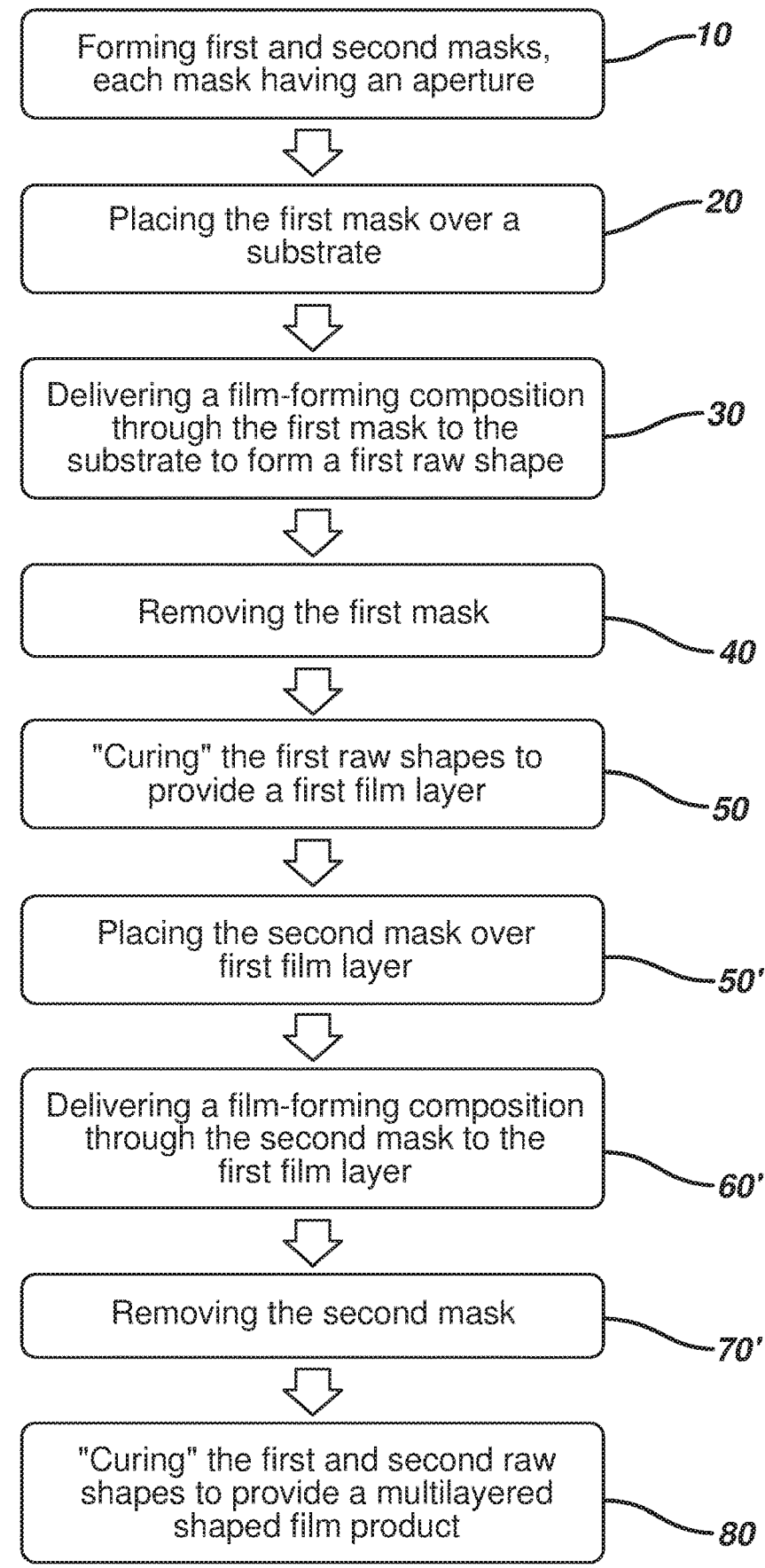

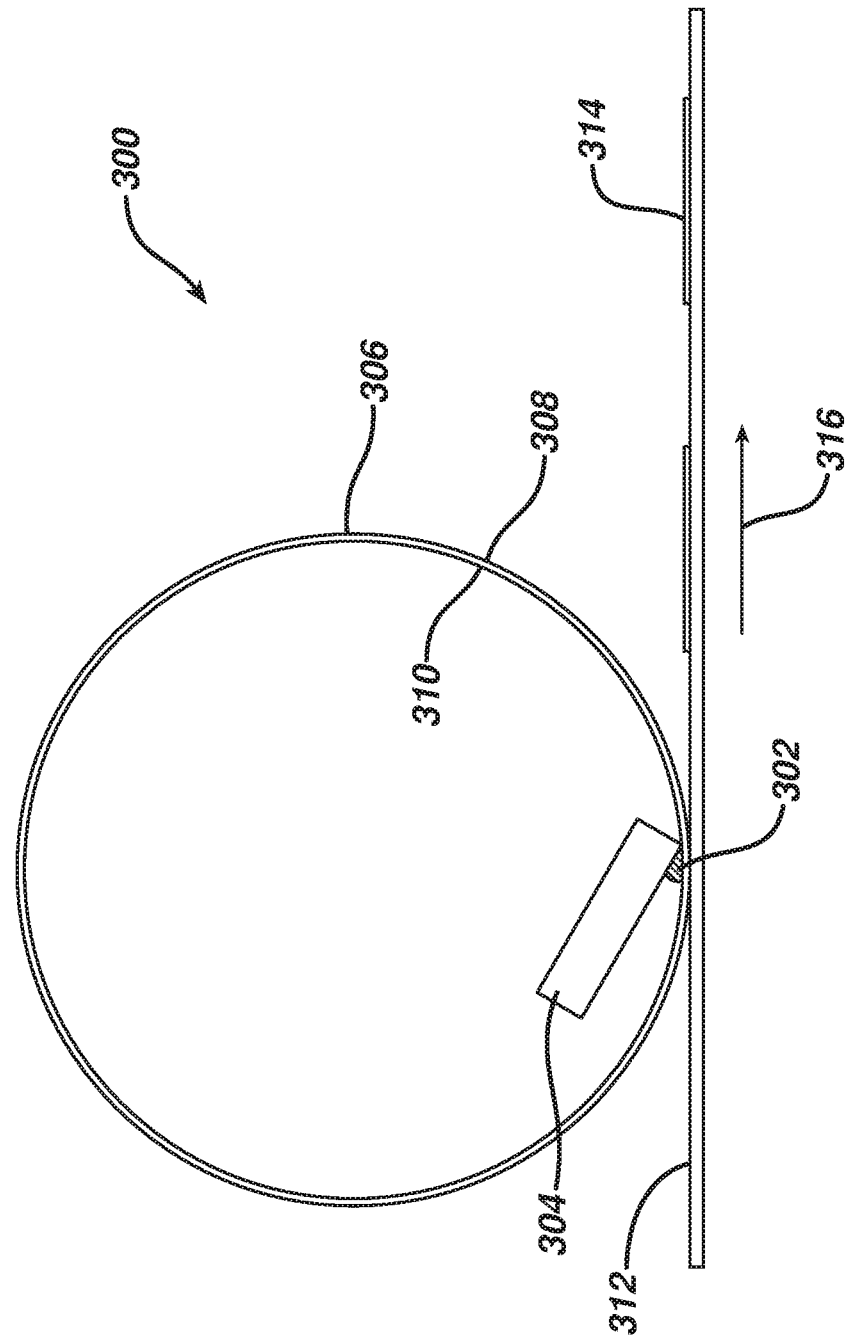

PROCESS FOR FORMING A MULTILAYERED SHAPED FILM PRODUCT

This application is a divisional of Ser. No. 14/580,977 filed on Dec. 23, 2014, and claims the benefit of provisional 61/922,296 filed on Dec. 31, 2013, the complete disclosure of which is hereby incorporated herein by reference for all purposes.

BACKGROUND

Film products have a wide variety of uses. These include decorative window decals, plasters, adhesive bandages, and oral strips (both medicated and otherwise).

Conventional production of such integral film products generally involves die-cutting the desired shaped product from film stock. While this production produces inexpensive film stock, die-cutting limits the efficiency and/or variability of final product forming. If the product shape is not completely rectangular or otherwise completely tessellated, the surrounding ladder scrap can produce significant waste. Therefore, products that have costly raw materials are often restricted to square or other completely tessellated shapes to substantially eliminate this expensive waste. This unfortunately prevents the formation of optimal shapes for some uses. Examples of die-cutting medical films include such production techniques are described in Pharmedica Ltd., WO 2012104834 A1, Pinna et al, U.S. Pat. No. 7,612,048 B2, and Smithkline Beecham Corp., WO 2005/009386 A2.

On the other hand, printing—including stencil printing and screen printing are known processes that are capable of providing irregular shapes on substrates. Generally, the printed materials remain permanently joined to the substrates, such as printed text and graphics on paper, printed circuits in the electronics industry, and printed designs on clothing and signage. However, such integration of a carrying substrate into a printed element prevents the usage of the printed product separate from the substrate.

What is needed is a process capable of commercial scale manufacturing of inexpensive, discrete film products without the waste of die-cutting and which products are capable of use independent of a supporting structure on which they are formed.

SUMMARY

Surprisingly, we have found a process capable of commercial scale manufacturing of inexpensive, multilayered shaped film product without the waste of die-cutting and which products are capable of use independent of a supporting structure on which they are formed. The process includes placing a first mask over a substrate; delivering a first film-forming composition through the first mask to form a first raw shape on the substrate; removing the first mask; placing a second mask or the first raw shape; delivering a second film-forming composition through the second mask to form a second raw shape on the first raw shape; removing the second mask; and solidifying the first and second raw shapes to provide the shaped film product disposed on the substrate.

BRIEF DESCRIPTION OF THE DRAWING

FIG. 4 is a plan view of a first screen mask capable of forming a first raw shape corresponding to the first layer of the multilayer product of FIG. 2.

FIG. 6 is a plan view of a second screen mask capable of forming a second raw shape corresponding to the second layer of the multilayer product of FIG. 2.

FIG. 8 is a block diagram of a process according to a modified embodiment of the present invention.

FIG. 10 is side elevation of a rotary printing system useful for forming the raw shapes corresponding to one or more layers of the multilayer product of the present invention.

DETAILED DESCRIPTION OF THE PREFERRED EMBODIMENTS

The present invention relates to a process and apparatus for forming multilayered shaped film products. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown but is to be accorded the widest scope consistent with the principles and features described herein. Multilayered shaped film products may have a wide variety of uses. These include household and recreational uses, such as decorative decals for windows and walls, temporary tattoos (such as body decals), healthcare devices such as medicated and/or absorbent plasters, adhesive bandages and other wound coverings, oral strips also known as a "consumable film" (medicated, therapeutic, and cosmetic), other body strips, such as moisturizing acne treatment, anti-wrinkle, dark circles, melisma, cellulite, delivery of vitamins, eczema, psoriasis, and the like.

As used herein the specification and the claims, the term "integral film product" variants thereof relate to a film product that is sufficiently robust to permit handling for a desired purpose separate from any supporting substrate. The product is removable from a substrate for use independent of the substrate.

As used herein the specification and the claims, the term "film-forming composition" variants thereof relate to a composition that is capable of forming, by itself or in the presence of an additional agent, a continuous film on a substrate.

As used herein the specification and the claims, the term "raw shape" variants thereof relate to the shaped volume of film-forming composition disposed on a substrate through an apertured mask. The raw shape generally requires further processing, such as integration, to transform it into an integral film product.

As used herein the specification and the claims, the term "solidification" variants thereof relate to the phase change from liquid to solid, can be through evaporation of a solvent, lowering of temperature, polymerization, cross-linking, and the like.

As used herein the specification and the claims, the term "tessellated" and variants thereof relate to a planar surface having a pattern of flat shapes having no overlaps or gaps. Thus, there is no "ladder waste" between the shapes.

Figure 1:
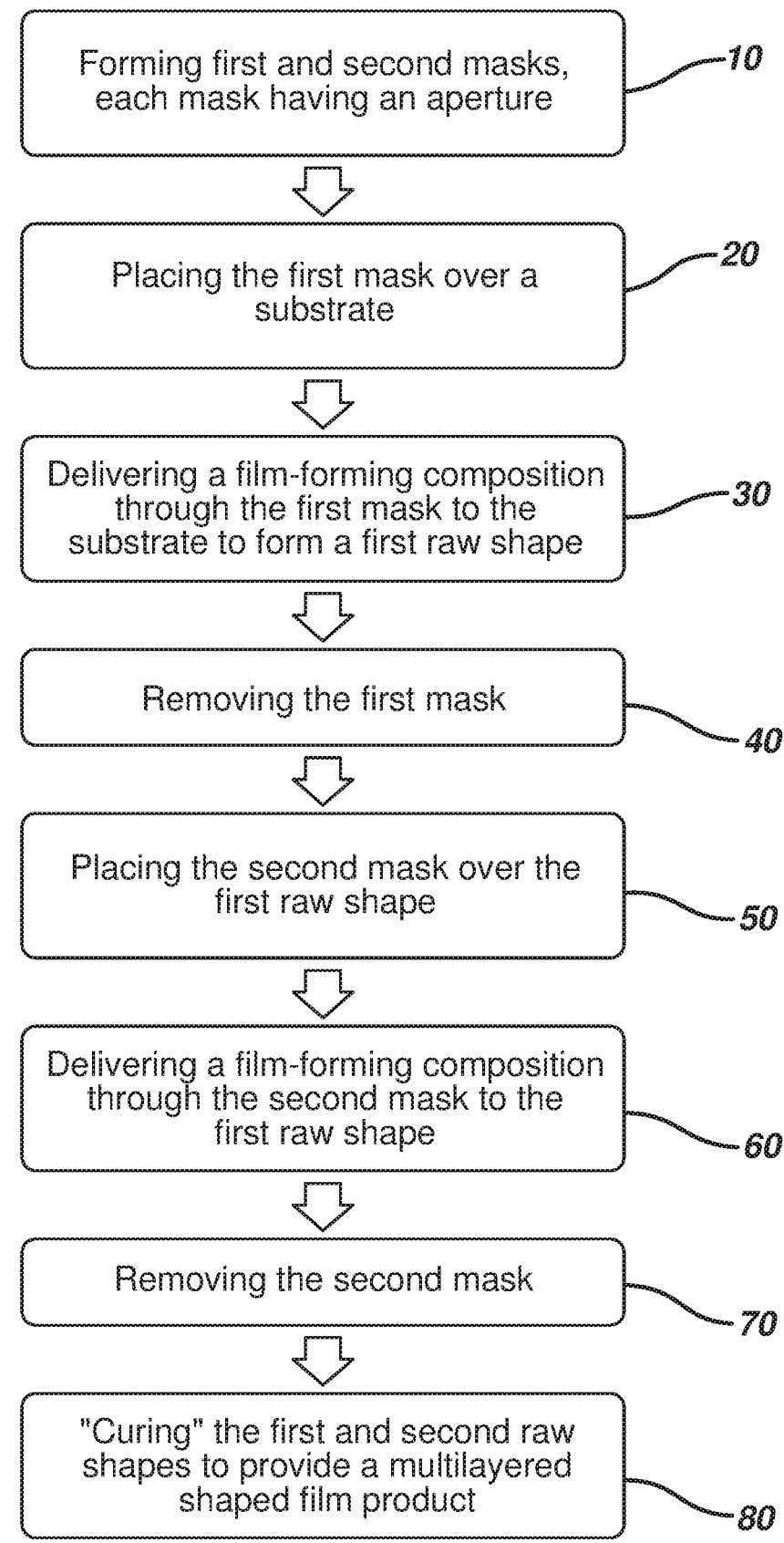
FIG. 1 is a block diagram of a process according to one embodiment of the present invention.

Referring to the drawing, FIG. 1 is a high level flow chart of a process for forming multilayered shaped film products. A first Step 10 includes forming first and second masks, each mask having an aperture. A second Step 20 includes placing the first mask over a substrate. A third Step 30 includes delivering a film-forming composition through the first mask to the substrate to form a first raw shape. A fourth Step 40 includes removing the first mask. A fifth Step 50 includes placing the second mask over the first raw shape. A sixth Step 60 includes delivering a film-forming composition through the second mask to the first raw shape to form a second raw shape. A seventh Step 70 includes removing the second mask. An eighth Step 80 includes solidifying the raw shape(s) by transforming the film-forming material(s) into the multilayered shaped film product.

Figure 2:
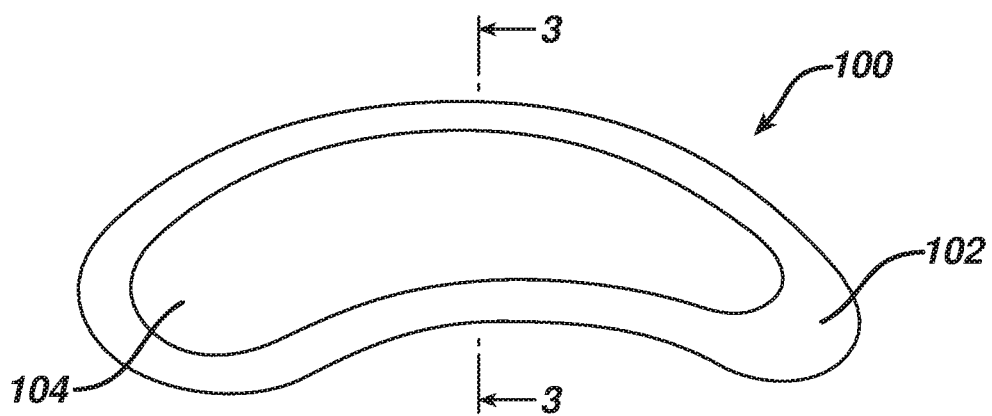
FIG. 2 is a plan view of a multilayer film product according to an embodiment of the present invention.
Figure 3:
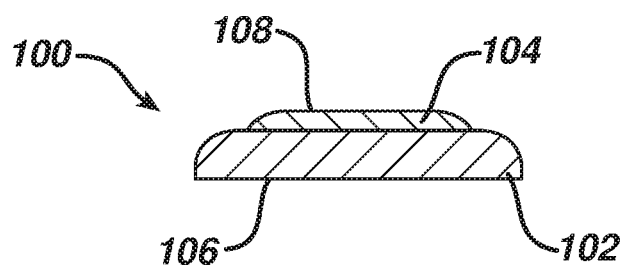
FIG. 3 is a cross-section along lines 3-3 of FIG. 2.

A multilayered film product 100 according to one embodiment of the invention is shown in FIGS. 2 and 3. In this embodiment, a first layer 102 has a larger surface area than a second layer 104 disposed on the upper surface of the first layer 102. This forms an "island" of the second layer 104 on top of the first layer 102. As shown in FIGS. 2 and 3, the innovations of the present invention allow the shape to be as simple or complex as desired. In one advantage of the present invention, the shape can be relatively complex—the kind of shape that would be very wasteful in a die-cutting operation with much ladder waste. For example, the minimum ladder waste produced during the printing of a pattern of nested circles is about 20% (based on circles arranged in straight columns and rows touching at the quadrants).

In reference to the embodiment of FIGS. 2 and 3, Step 10 involves forming a first mask and a second mask, each mask having at least one aperture corresponding to the first and second raw shape, respectively.

Print masks are known in the art. They can include without limitation stencils, screens, meshes, tapes, and the like. While the exact fabrication of the print masks is not critical to the present invention, our invention makes is possible to form relatively thick integral film products and therefore, use relatively thick masks. Preferably, the mask has a thickness of at least about 0.05 millimeters ("mm"). In one embodiment for use on the skin for flexible, relatively unnoticeable products, the mask has a thickness of between about 0.05 mm and about 0.3 mm, more preferably, between about 0.1 and about 0.2 mm. In another embodiment, thick integral film products can be made using a mask having a thickness of greater than about 0.2 mm, preferably between about 0.2 and about 2 mm, preferably between about 0.4 mm and about 1 mm, and most preferably between about 0.5 mm and about 1 mm. In many embodiments, the thickness of the mask is not critical, while in other embodiments, the present invention makes possible the formation of integral film products with previously unknown thicknesses.

The thickness of the mask generally determines the maximum thickness of the integral film product. The relationship is determined by the nature of the film-forming composition and the mechanism by which the composition solidifies. For example, hot melt and hydrocolloid film-forming compositions generally produce a product thickness that is essentially equivalent to the mask thickness. Foaming film-forming compositions can also be used and may provide solidified films having a thickness substantially equivalent to the thickness of the mask, or possibly even thicker. Solvent or other carrier-based compositions will lose thickness as the product solidifies. The reduction in thickness is generally related to the solids content of the composition. We have found that a solids content of 30-40% delivers an integral film product having a thickness of about 50% of the mask thickness. Formulations with lower solids content would likely deliver final products having a thickness of even less than 50% of the mask thickness.

For example, a stencil mask thickness of 0.5 mm would be capable of depositing a raw shape of film-forming composition of about 0.5 mm. Upon transformation into the integral film product, the thickness would diminish, based upon the solids content of the film-forming composition.

Different mesh sizes are used for different applications in the screen printing process. The mesh geometry will define the characteristics of the mesh. Screen mesh geometry is defined by the mesh count and thread diameter. The mesh count refers to the number of threads per inch contained in the mesh. The thread diameter refers to the diameter of the thread before it has been woven into the mesh. The thread diameter and mesh count together determine the mesh opening. Mesh opening is the spacing between the adjacent threads. Mesh openings dictate the maximum particle size that can be used, and affects the overall detail printed as well as the formula release characteristics. For optimum film-forming composition passage through the mesh the maximum particle size must be smaller than about ⅓ of the mesh opening.

Some typical mesh sizes and the pore openings associate with them are:

| Micron | U.S. Mesh |
|---|---|
| 2000 | 10 |
| 1000 | 18 |
| 500 | 35 |
| 250 | 60 |
| 149 | 100 |
| 125 | 120 |
| 105 | 140 |
| 74 | 200 |
| 53 | 270 |
| 37 | 400 |

The choice of materials is not critical in the production of the print masks of the present invention. Those of ordinary skill in the art will recognize that masks can be made of structural materials, including without limitation: metals, such as aluminum alloy, stainless steel, Ni alloy, Cr alloy or the like; resins, such mask as polyimide, polyester, epoxy, polycarbonate, polyethylene, polyethylene terephthalate (PET), polypropylene or the like; glass; paper; wood; or cardboard, as well as combination thereof. As another example, the mask body may be made of a composite material, such as glass fiber filled polyimides, polyesters, or epoxies. The mask body is formed in a sheet from these materials. The thickness of the sheet may be from 20 to 2000 microns (µm), although for ease in handling and other considerations, the thickness is preferably from 20 to 80 µm.

An example of a mask according to one embodiment of the present invention, useful in the formation of the multi-layered shaped film product 100 of FIGS. 2 and 3 is a first screen mask 200 shown in FIG. 4 that may be used in flatbed screen printing apparatus. The first screen mask 200 includes an impermeable mask portion 202 which defines at least one aperture 204 with an exposed screen (or mesh) 206.

Figure 5:
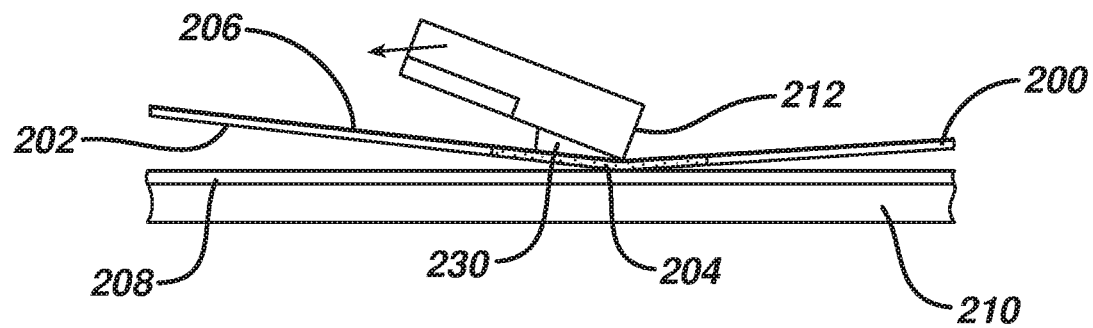
FIG. 5 is side elevation of a screen printing system for forming the first raw shape corresponding to the first layer of the multilayer product of FIG. 2.

With reference to FIG. 5, the first mask 200 is placed over a substrate 208 in Step 20. This substrate 208 may be an endless belt (a continuous flexible web, linked platens, and the like), or it may be a web that carries the resulting multilayer product. The resulting multilayer product may be permanently attached to the web, or it may be releasably attached to a web, such as a release liner. Surfaces may be modified through the use of dry film lubricants such as molybdenum disulfide, graphite, tungsten disulfide or oils that are generally known to those of ordinary skill in the art. Typical release surfaces may include silicone, polytetrafluoroethylene (PTFE), waxes, polymers, polished metals, or combinations thereof. The process may employ flatbed apparatus or rotary apparatus. The printing apparatus will have a support for a substrate and system for delivering a film-forming composition through the first mask (Step 30).

Delivery systems often include a conduit to provide the film-forming composition to the mask and a device to urge the composition to the mask aperture. Such devices include blade-like structures (also called knives, squeegees, doctor blades, wiper blades, wipers, and the like), nozzles and the like. The blade angle generally determines the relative force applied to move the composition into the mask aperture and to the substrate. The blade angle (the included angle defined by the blade and upper mask surface) will be optimized to work with the flow characteristics of the film-forming composition. Too small of an angle can starve the interface between blade and upper mask surface of film-forming composition, and too large of an angle will not provide sufficient pressure to deliver the composition into the mask aperture. In one embodiment of the invention, the blade angle is preferably less than about 45°, more preferably, between about 20° and 40°. A low blade angle, less than about 30°, works better for pushing more material in order to fill a thicker stencil. Pressurized nozzles can also be used which supply a material under constant pressure in order to fill the stencil.

In the embodiment of FIG. 5, a simple flatbed screen system incorporates a flatbed support 210 for the substrate 208, a simple, flat mask 200, and a squeegee 212. In this process, the film-forming composition is deposited onto the screen 206, and the squeegee 212 wipes the film-forming composition across the screen 206. The relative movement of the squeegee 212 with respect to the screen 206 forces the film-forming composition through the screen 206. The mask portion 202 associated with the screen 206 defines one or more apertures 204 of a desired shape. The thickness of the mask 200 generally defines the thickness of the first layer of the resulting multilayer film product (accounting for some shrinkage during the finishing Step 80, described below. The mask 200 comes into contact with the substrate 208 due to the squeegee pressure and forms a localized seal to the substrate to prevent escape of the film-forming composition from the desired shape. The screen 206 and surface of the substrate 208 are selected to provide a greater surface affinity between the film-forming composition and the substrate surface than between the film-forming composition and the screen.

Figure 7:
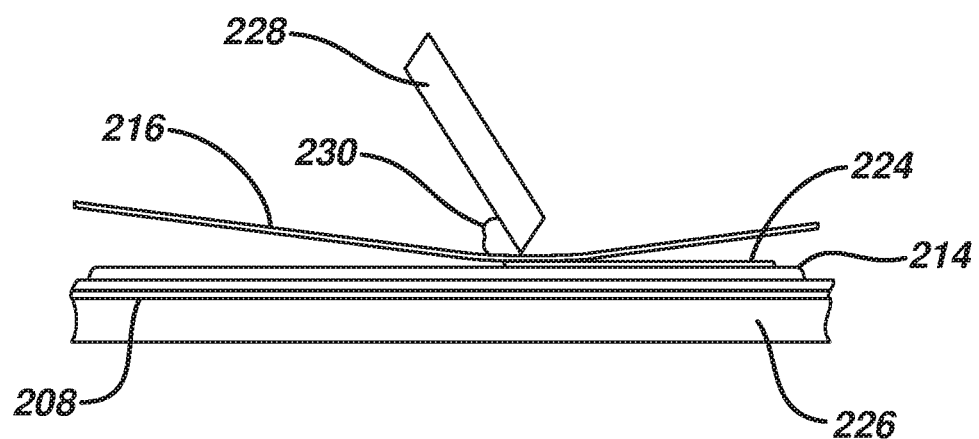
FIG. 7 is side elevation of a screen printing system for forming the second raw shape corresponding to the second layer of the multilayer product of FIG. 2.

In step 40, the first mask 200 is removed leaving a first raw shape 214 deposited on the substrate 208, corresponding to the first layer 102 of the multilayered film product 100. In step 50 a second screen mask 216, including an impermeable mask portion 218 which defines at least one aperture 220 exposing a screen (or mesh) 222, is placed over the first raw shape 214 (as shown in FIG. 7). The at least one aperture 220 of the second screen mask 216 defines a second raw shape 224 corresponding to the second layer 104 of the multilayered film product 100.

Again, a simple flatbed screen system may be used in forming the second layer of the multilayer product. The system includes a second flatbed support 226, which accommodates the substrate 208 and first raw shape 214, the second screen mask 216, and a squeegee 228. In this process, a film-forming composition 230 is deposited onto the mask 218, and the squeegee 228 wipes the film-forming composition across the mask 218 and screen 222 in step 60. Again, the relative movement of the squeegee 228 with respect to the screen 222 forces the second film-forming composition 230 through the screen 222 to contact the first raw shape 214. The blade angle and screen mesh properties (count and % opening) determine the second layer thickness of the resulting multilayer film product (accounting for some shrinkage during the finishing Step 80, described below. Unlike in during the formation of the first raw shape 214, the impermeable mask portion 218 is not substantially thicker than the screen 222 associated therewith, and the second screen mask 216 does not contact the first raw shape 214. The screen is held at a fixed distance above the first raw shape. The downward pressure of the squeegee deflects the screen closer to the first raw shape such that the second film-forming composition forced through the screen contacts the first raw shape and transfers the second film-forming composition from the screen to the top surface of the first raw shape. In this manner, there is no opportunity for the second screen mask 216 to disrupt the first raw shape 214. The screen 222, the second film-forming composition 230 and the first film-forming composition are selected to provide a greater surface affinity between the two film-forming compositions than between the second film-forming composition 230 and the screen 222.

As the second screen mask 216 is removed in step 70, a raw multilayer product including the first raw shape 214 and the second raw shape 224 defined by the second screen mask 216, remains.

In step 80, the raw multilayered shape is transitioned into the multilayered film product 100. Again, the multilayered film product 100 may be permanently attached to the substrate 208, or the substrate 208 may be a release liner to permit the product to be removed therefrom for use independent of the substrate. The exact nature of the finishing station is not critical to the present invention. Indeed, one of ordinary skill in the art will recognize that the raw shapes may be transformed into finished film layers and/or the complete multilayered film product thorough any number of process steps, depending upon the nature of the film-forming composition, as described in more detail, below. For example, the raw shapes may be heated to drive off volatile carriers, such as such as water and organic solvents. Alternately, the finishing can be through providing energy, such as UV light to cross-link or otherwise "cure" one or more polymeric film-forming components. If one or more film-forming components is a hot melt composition, the finishing can be as simple as allowing the raw shape to cool below a melt or glass transition temperature.

In addition, one of ordinary skill in the art will recognize that additional layers may be added by repeating steps 50 through 70 with additional film-forming compositions to provide multilayered film products having more than two layers.

Again, the resulting multilayered product may be permanently attached to the web, or it may be releasably attached to a web, such as a release liner. If the process according to the present invention employs a release lined web as the substrate, the release lined web may be used as a carrier and packaged with the integral film product in appropriate sized primary packaging until delivered to a consumer. The consumer may then remove the integral film product from the substrate and use it as desired. Alternately, if the process according to the present invention employs an endless belt having a releasable surface or other substrate integrated into the manufacturing equipment, the integral film product is removed from the releasable surface of the substrate and packaged for delivery to a consumer. The integral film product may have an adhesive surface, such as in a medicated plaster, or it may have non-tacky surfaces, such as in an oral strip.

Figure 9B:
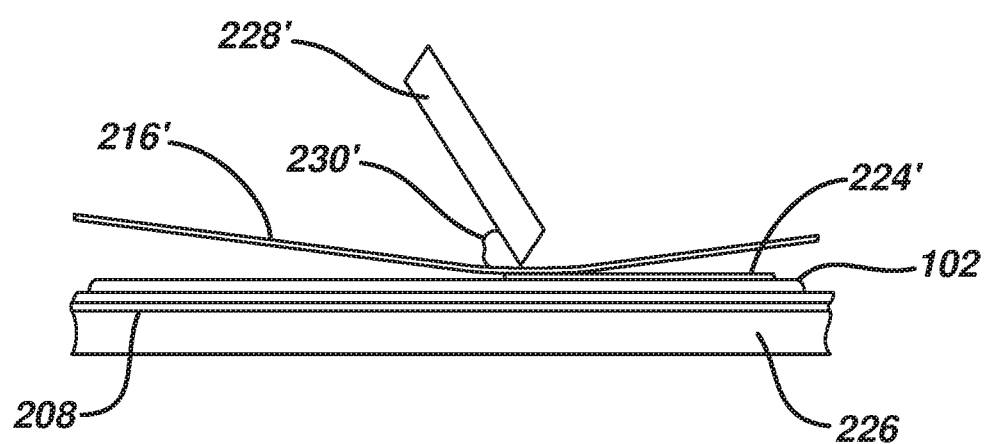
FIG. 9B is side elevation of a screen printing system for forming the second raw shape corresponding to the second layer of the multilayer product of FIG. 2 in the alternate process of FIG. 8.
Figure 9A:
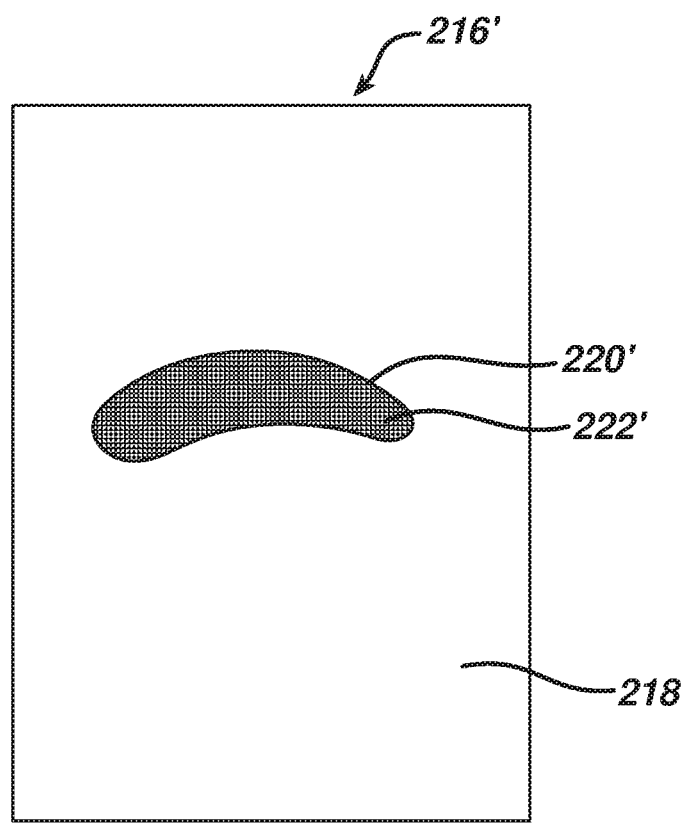
FIG. 9A is a plan view of a screen mask capable of forming a second raw shape corresponding to the second layer of the multilayer product of FIG. 2 in the alternate process of FIG. 8.

An alternative process shown as a block diagram in FIG. 8 may follow steps 10 through 40, as described above to form the first raw shape 214. This first raw shape 214 may then be "cured" to provide the first layer 102 of the multilayered film product 100 in step 45. Steps 50' through 70' may take place as follows:

In step 50' a second screen mask 216', including an impermeable mask portion 218' which defines at least one aperture 220' exposing a screen (or mesh) 222', is placed over the layer 102 (as shown in FIG. 9B). The at least one aperture 220' of the second screen mask 216' defines a second raw shape 224' corresponding to the second layer 104 of the multilayered film product 100.

Again, a simple flatbed screen system may be used in forming the second layer of the multilayer product. The system includes a second flatbed support 226', which accommodates the substrate 208 and first layer 102, the second screen mask 216', and a squeegee 228'. In this process, a film-forming composition 230' is deposited onto the screen 222', and the squeegee 228' wipes the film-forming composition across the screen 222' in step 60'. Again, the relative movement of the squeegee 228' with respect to the screen 222' forces the second film-forming composition 230' through the screen 222' to contact the first layer 102. The configuration of the second screen mask 216' generally defines the thickness of the second layer 104 of the resulting multilayer film product 100 (accounting for some shrinkage during the finishing Step 80, described below. Unlike the formation of the second raw shape 224, described in the previous embodiment, the second screen mask 216' may contact the first layer 102, as it is already "cured". The screen 222', the second film-forming composition 230' and the first layer 102 are selected to provide a greater surface affinity between the first layer 102 and the second film-forming composition 230' than between the second film-forming composition 230' and the screen 222'.

As the second screen mask 216' is removed in step 70', a multilayer structure including the first layer 102 and the second raw shape 224 defined by the second screen mask 216, remains.

In step 80', the multilayered structure is transitioned into the multilayered film product 100. Again, the multilayered film product 100 may be permanently attached to the substrate 208, or the substrate 208 may be a release liner to permit the product to be removed therefrom for use independent of the substrate.

One of ordinary skill in the art will recognize that additional layers may be added by repeating steps 45 through 80' with additional film-forming compositions to provide multilayered film products having more than two layers, finishing the raw shapes between applications of film-forming compositions.

The above processes are described with reference to flatbed stencil printing systems. However, one of ordinary skill in the art will recognize that variations may be made to the process. For example, the first layer (first raw shape) may be formed using a stencil—a mask without the screen or mesh disposed across the at least one aperture. One or more printing steps may also be performed on a rotary printing system 300 as shown in FIG. 10. In this system, the film-forming composition 302 may be applied with a nozzle or a squeegee 304. The printing drum 306 includes a mask 308 having an aperture formed on a screen 310. The mask 308 forms the outer surface of the drum 306, while the screen 310 is on the inner surface of the printing drum 306, and the aperture is in fluid communication with the interior of the drum. The film-forming composition is delivered to the interior of the drum 306 via a conduit and delivered to the inner surface of the screen 310. The squeegee 304 transfers the film-forming composition to the screen 310 and then to the substrate 312 as described above. The first raw shape 314 then moves in the direction of arrow 316 for further processing.

In addition, if the first raw shape is solidified prior to the addition of the second film-forming composition, the second printing step may also employ a stencil without the screen, when using a flatbed stenciling process.

Figure 11:
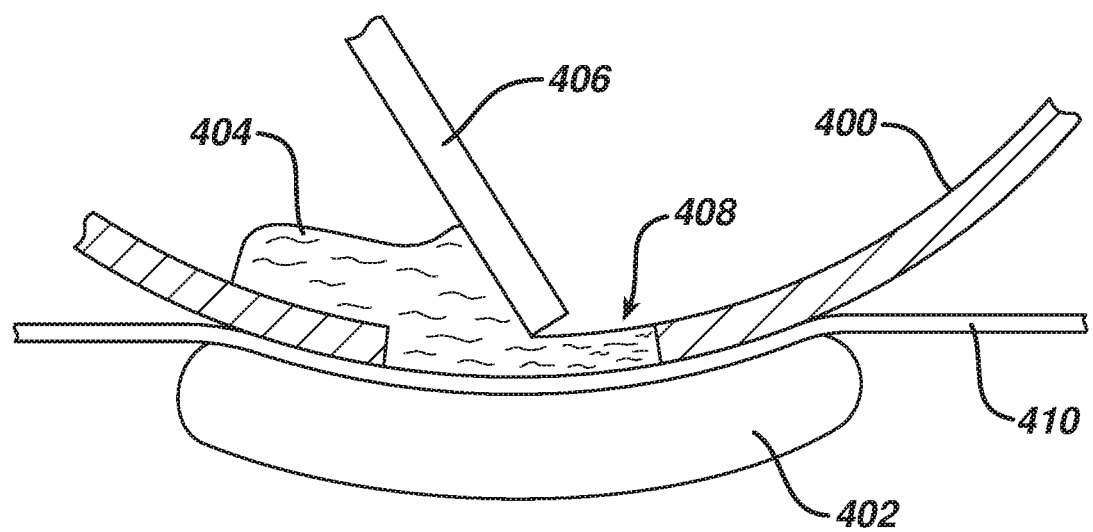
FIG. 11 is side elevation of a rotary printing system useful for forming the raw shapes corresponding to one or more layers of the multilayer product of the present invention.

In an alternate embodiment, a rotary stencil 400 may require a concave substrate support 402 to prevent uncontrolled escape of the film-forming composition 404 until the squeegee 406 forces it through the stencil aperture 408. The substrate 410 thus wraps around the outer diameter of the printing drum to contain the stencil volume. A rigid blade may be used in place of a flexible squeegee as shown in FIG. 11.

Figure 12A:
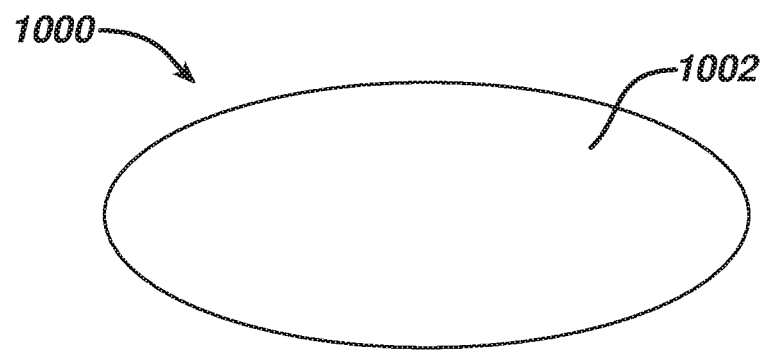
FIG. 12A is a top plan view of an alternate embodiment of a multilayer film product according to the invention.
Figure 12B:
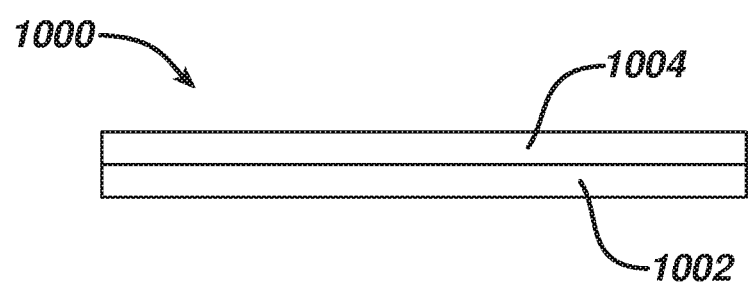
FIG. 12B is a side elevation of the multilayer film product of FIG. 12A.

The process of the present invention may be used to form many different forms of multilayered shaped film products. For example the multilayer film product of FIGS. 2 and 3 may be modified as shown in FIGS. 12A and B in which the first and second layers 1002 and 1004 are substantially co-extensive. This multilayered shaped film product 1000 may be formed substantially as described above.

Figure 13A:
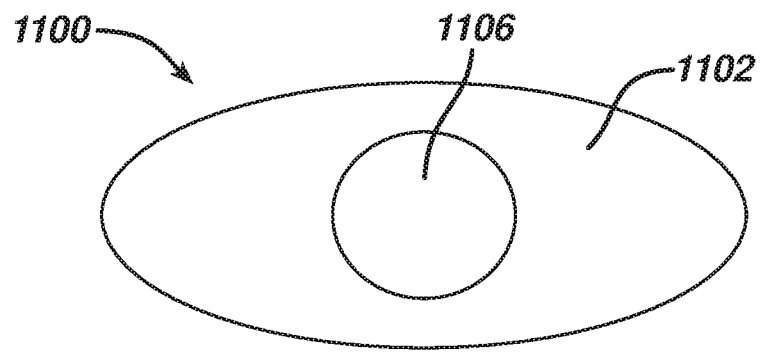
FIG. 13A is a bottom plan view of an alternate embodiment of a multilayer film product according to the invention.
Figure 13B:
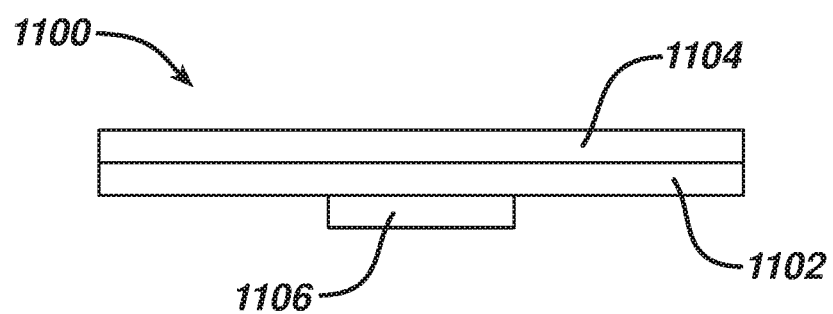
FIG. 13B is a side elevation of the multilayer film product of FIG. 13A.

An alternative embodiment is shown in FIGS. 13A and B in which the "island" of the embodiment of FIGS. 2 and 3 is placed on the bottom layer of the embodiment of FIGS. 12A and B. Thus, the first and second layers 1102, 1104 are coextensive, and the third layer 1106 forming the "island" is formed on bottom to form a three-layered multilayered shaped film product 1100. In this embodiment, the top layer 1104 may be integrated prior to formation of the middle and bottom layers 1102,1106, or all three layers may be formed deposited prior to integration. Preferably, the middle and bottom layers 1102,1106 are formed by screen-printing.

Figure 14A:
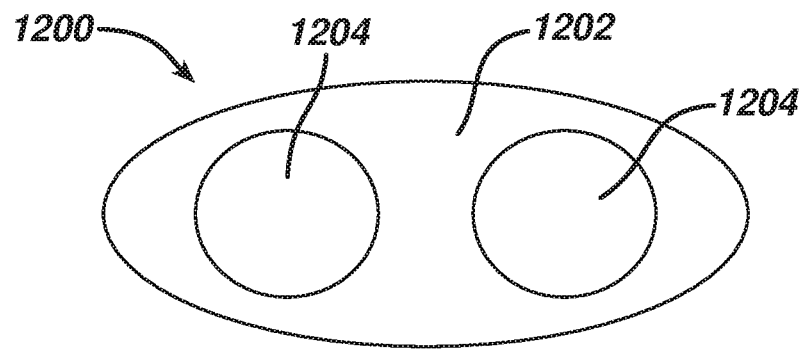
FIG. 14A is a bottom plan view of an alternate embodiment of a multilayer film product according to the invention.
Figure 14B:
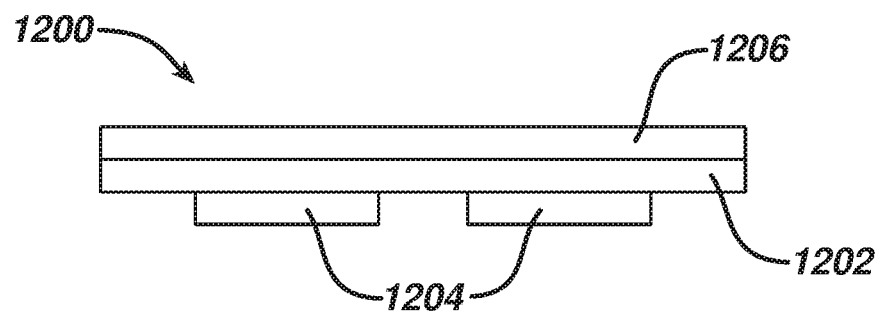
FIG. 14B is a side elevation of the multilayer film product of FIG. 14A.

Another alternate embodiment is shown in FIGS. 14A and B incorporates two separate islands. In this embodiment, the multilayered shaped film product 1200 has a first layer 1202 and a pair of islands 1204 as the second layer. If desired a third layer 1206 may also be included. The islands 1204 may have identical film materials or film materials that differ from one another (the film material(s) resulting from the transformation of the film-forming composition(s) into a film structure). Of course, more than two islands can be incorporated in this product form.

Figure 15A:
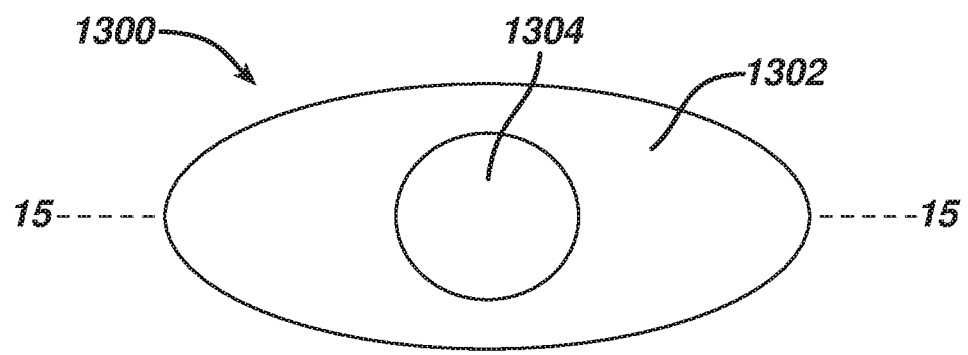
FIG. 15A is a bottom plan view of an alternate embodiment of a multilayer film product according to the invention.
Figure 15B:
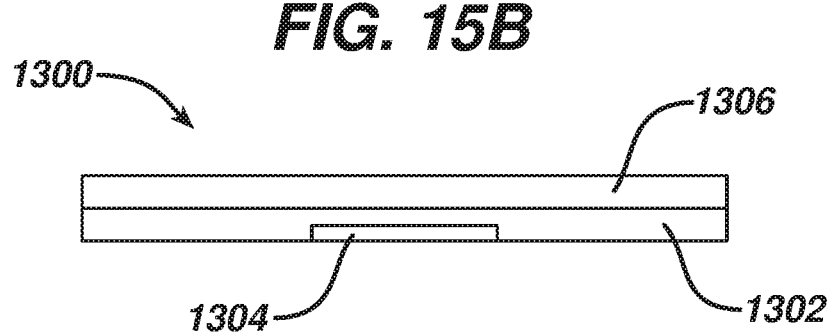
FIG. 15B is a cross-section of the multilayer film product of FIG. 15A along line 15-15.
Figure 15C:
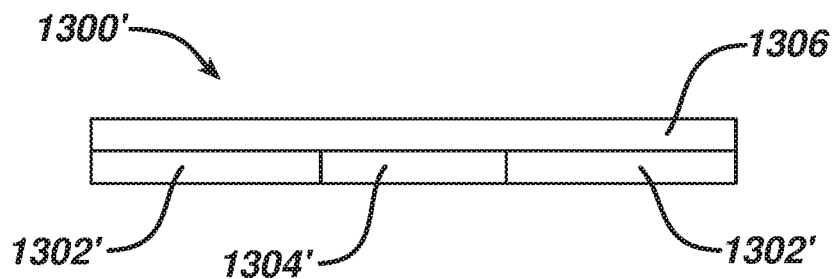
FIG. 15C is a cross-section of the modified multilayer film product of FIG. 15A along line 15-15.

In the alternative embodiment of FIGS. 15A and B, the multilayered shaped film product 1300 has a first layer 1302 formed about and covering a pre-formed island 1304. An optional second layer 1306 may be formed on the surface of the first layer 1302 opposite the pre-formed island 1304. In this process, the island 1304 may be formed and then integrated into a solid structure and the first layer 1302 may be created by stenciling, as described above. The optional second layer 1306 may be formed after integration of the first layer 1302 or may be screen-printed on a wet first layer 1302. As shown in the embodiments of FIGS. 15A and B, the pre-formed island 1304 is thinner than the first layer 1302. One of ordinary skill in the art would recognize that the thickness of these elements could be balanced to provide a first layer 1302' encircling the preformed island 1304', while the optional second layer 1306 contacts both the first layer 1302' and preformed island 1304' as shown in FIG. 15C.

Figure 16A:
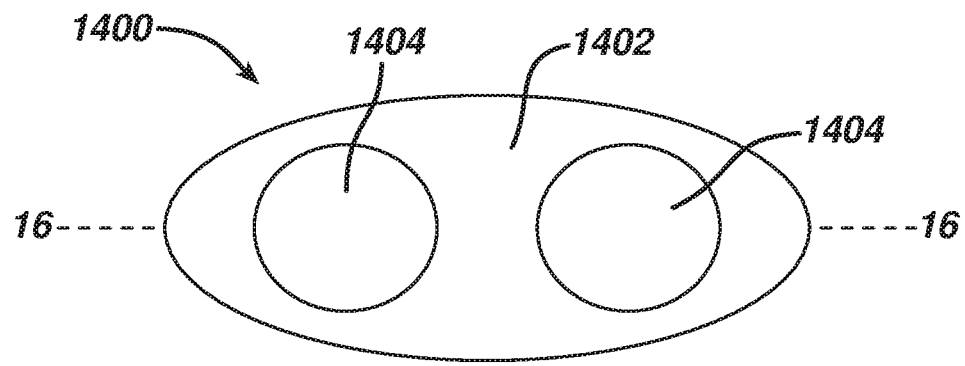
FIG. 16A is a bottom plan view of an alternate embodiment of a multilayer film product according to the invention.
Figure 16B:
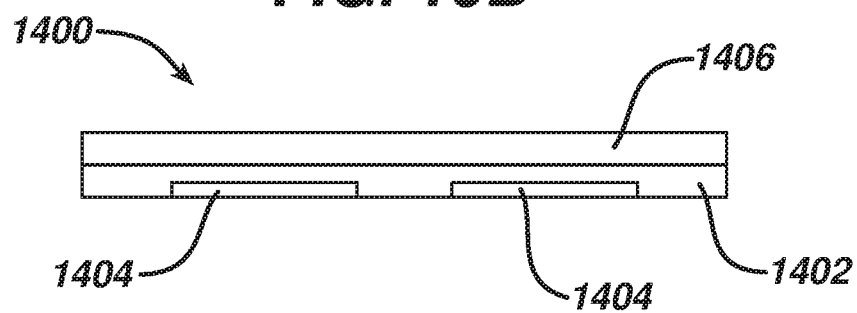
FIG. 16B is a cross-section of the multilayer film product of FIG. 16A along line 16-16.
Figure 16C:
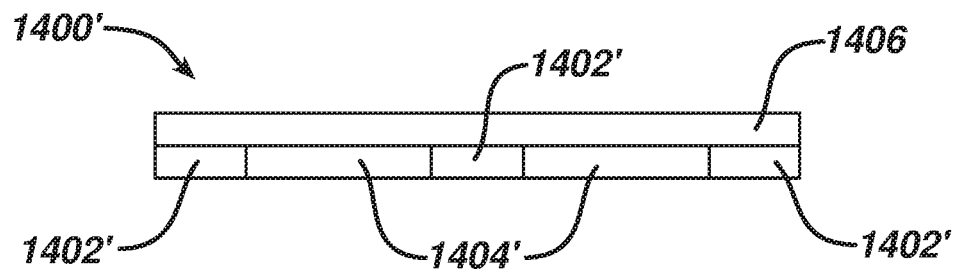
FIG. 16C is a cross-section of the modified multilayer film product of FIG. 16A along line 16-16.

A similar process may be used to form the multilayered shaped film product 1400 of embodiment of FIGS. 16A and B. Again, the first layer 1402 may be formed about and covering a plurality of pre-formed islands 1404. An optional second layer 1406 may be formed on the surface of the first layer 1402 opposite the pre-formed islands 1404. The islands 1404 may have identical compositions or compositions that differ from one another. Of course, more than two islands can be incorporated in this product form. Again, one of ordinary skill in the art would recognize that the thickness of these elements could be balanced to provide a first layer 1402' encircling the preformed islands 1404', while the optional second layer 1406 contacts both the first layer 1402' and preformed islands 1404' as shown in FIG. 16C.

Figure 17A:
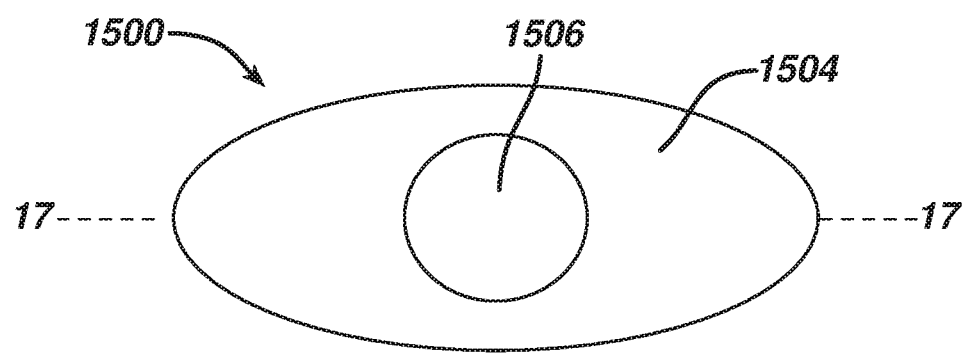
FIG. 17A is a bottom plan view of an alternate embodiment of a multilayer film product according to the invention.
Figure 17B:
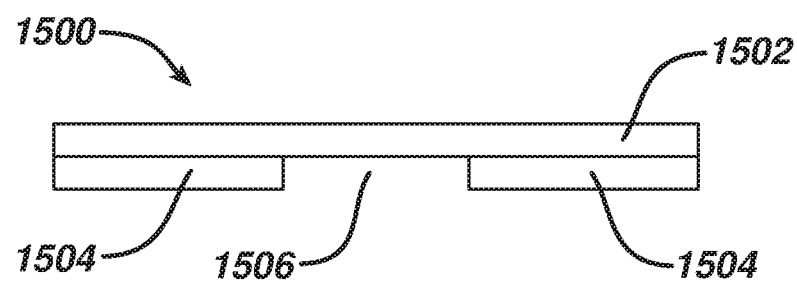
FIG. 17B is a cross-section of the multilayer film product of FIG. 17A along line 17-17.

A multilayered shaped film product 1500 having a void in one layer is shown in FIGS. 17A and B. This may be produced by forming a continuous, first layer 1502 and subsequently screen-printing a second layer 1504 having a void 1506 defined therein. In use, this product could be applied via either the first layer 1502 or the second layer 1504. For example, the multilayered shaped film product 1500 may be a corn pad, and in use, it would be applied such that the corn is located in the void 1506.

In each of the foregoing embodiments, the different film-forming compositions may be employed for each discrete portion of the multilayered shaped film product, or the same film-forming composition could be provided to multiple portions of the product.

In the embodiments of the present invention in which the second layer is formed on the first layer prior to the solidification of the first layer, the compatibility of film-forming compositions is very important. If there is a significant difference between the film-forming compositions, there can be a driving force at the molecular level that will generate film defects such as holes, voids, ribbing, and wrinkles. One significant characteristic of the film-forming compositions is polarity. Water is a polar molecule. Oil is a non-polar molecule. The two don't mix and they will repel each other. Two measures of polarity are solubility and surface energy. Solubility is the amount of solid dissolving in a liquid to form a homogeneous solution; it is typically quantified in gm/kg (solute/solvent). Liquid materials have a driving force at the boundary of the surface called surface energy. The energy level is measured by the surface contact angle. Film-forming compositions with similar solubility and surface energy will not have repelling forces.

The viscosity of the film-forming compositions can also play a significant role. High viscosity materials will resist repelling forces better than low viscosity materials. The typical viscosity measurement is dynamic sheer, often measured with a Brookfield Viscometer.

The film-forming compositions employed in the present invention may be in the form of a hot melt composition, a solid material that can be melted to form a flowable liquid and deposited to form a raw shape which can then cool to form the shaped multilayered film product. Alternatively, the film-forming composition may include at least a film forming component and a carrier. Additional components may include, without limitation, emulsifiers, surfactants, plasticizers, active ingredients, fragrances, coloring agents, flavorings, and other components known to those of ordinary skill in the art. The carrier is preferably a liquid and may be a solvent or diluent. Preferred carriers include water and alcohols.

The water soluble polymers of the present invention possess film forming properties useful producing the films of the present invention. Many water soluble polymers may be used in the films of the present invention. A representative, non-limiting list includes pullulan, cellulose ethers (such as hydroxypropylmethyl cellulose, hydroxyethyl cellulose, hydroxypropyl cellulose), polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymers, carboxyvinyl polymers, amylose, starches (such as high amylose starch and hydroxypropylated high amylose starch), dextrin, pectin, chitin, chitosan, levan, elsinan, collagen, gelatin, zein, gluten, soy protein isolate, whey protein isolate, casein and/or mixtures thereof.

In one preferred embodiment, the carrier is water. In alternate embodiments, organic solvents which have been conventionally used can be employed as the solvent. A representative, non-limiting list of useful solvents includes monovalent alcohols such as methanol, ethanol, propanol, butanol, 3-methoxy-3-methyl-1-butanol, and 3-methoxy-1-butanol; alkylcarboxylic acid esters such as methyl-3-methoxypropionate, and ethyl-3-ethoxypropionate; polyhydric alcohols such as ethylene glycol, diethylene glycol, and propylene glycol; polyhydric alcohol derivatives such as ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, ethylene glycol monomethyl ether acetate, ethylene glycol monoethyl ether acetate, and propylene glycol monomethyl ether acetate; fatty acids such as acetic acid, and propionic acid; ketone such as acetone, methyl ethyl ketone, and 2-heptanone. These organic solvents may be used alone, or in combination.

The film product may also contain at least one surfactant, including anionic, amphoteric, non-ionic, and cationic surfactants or mixtures thereof.

A representative, non-limiting list of anionic surfactants includes, alone or mixed, salts (for example salts of alkali metals, such as of sodium, ammonium salts, salts of amines, salts of amino-alcohols or magnesium salts) of the following compounds: alkyl sulphates, alkylether sulphates, alkylamidoether-sulphates, alkylarylpolyether-sulphates, monoglyceride sulphates, alkyl sulphonates, alkyl phosphates, alkylamide sulphonates, alkaryl sulphonates, α-olefin sulphonates, paraffin sulphonates; alkyl sulphosuccinates, alkylether sulphosuccinates, alkylamide-sulphosuccinates, alkyl sulphosuccinamates, alkyl sulphoacetates, alkylether phosphates, acyl sarcosinates, acyl isethionates and N-acyl taurates, the alkyl or acyl radical of all these various compounds for example having from 8 to 24 carbon atoms, and an aryl radical such as a phenyl or benzyl group.

According to at least one embodiment, the salts include those of fatty acids, such as the salts of oleic, ricinoleic, palmitic, stearic acids, acids of copra oil or of hydrogenated copra oil, acyl lactylates whose acyl radical has 8 to 20 carbon atoms, alkyl D-galactoside uronic acids and their salts as well as the polyoxyalkylenated alkyl(C6-C24)ether carboxylic acids, the polyoxyalkylenated alkyl(C6-C24)aryl ether carboxylic acids, the polyoxyalkylenated alkyl(C6-C24)amido-ether carboxylic acids and their salts, for example those having from 2 to 50 ethylene oxide groups, and mixtures thereof.

A representative, non-limiting list of amphoteric surfactants includes, alone or mixed, the derivatives of secondary or tertiary aliphatic amines wherein the aliphatic radical is a linear and branched chain with 8 to 22 carbon atoms and comprises at least one hydrosolubilizing anionic group (for example carboxylate, sulphonate, sulphate, phosphate or phosphonate); the alkyl (C8-C20) betaines, the sulphobetaines, the alkyl (C8-C20) amidoalkyl (C1-C6) betaines such as cocoamidopropyl betaine or the alkyl (C8-C20) amidoalkyl (C1-C6) sulphobetaines.

A representative, non-limiting list of non-ionic surfactants includes, alone or mixed, alcohols, alpha-diols, alkyl phenols or polyethoxylated, polypropoxylated or polyglycerolated fatty acids, having an aliphatic chain with for example 8 to 18 carbon atoms, where the number of ethylene oxide or propylene oxide groups can optionally be in the range from 2 to 50 and the number of glycerol groups can optionally be in the range from 2 to 30.

Any plasticizer known in the pharmaceutical art is suitable for use in the film product. These include, but are not limited to, polyethylene glycol; glycerin; sorbitol; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof.

The film product of the present invention may also contain at least one colorant, such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the cosmetic compositions of the invention will depend on the color, intensity and use of the cosmetic composition and, as a result, will be determined by those skilled in the art of cosmetic formulation.

Any thickener known in the art may optionally be added to the film. Suitable thickeners include, but are not limited to, cyclodextrin, crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are suitable and are exemplified by xylitol and erythritol, respectively.

Preservatives known in the art may optionally be added to the film. Suitable Preservatives include, but are not limited to Benzalkonium Chloride, Benzyl Alcohol, 2-Bromo-2-Nitropropane, Butylparaben, Chlorhexidine Digluconate, Chlorphenism, Dehydroacetic Acid, Citric Acid, Diazolidinyl Urea, DMDM Hydantoin, Ethylparaben, Formaldehyde, Imidazolidinyl Urea, Isobutylparaben, Methylisothiazolinone, Methylparaben, Phenoxyethanol, Polyaminopropyl biguanide, Potassium Sorbate, Propylparaben, Quaternium-15, Salicylic Acid, Sodium benzoate, Sodium Dehydroacetate, Sodium Metabisulfite, Sodium Salicylate, Sodium Sulfite, Sorbic Acid, Stearalkonium Chloride, Triclosan, and Zinc Pyrithione.

In some embodiments, "microbeads" or other particulate materials may be incorporated and used as "scrubbing particles" or "exfoliates" in film products used in personal care products such as facial scrubs and body washes. The microbeads are small particles, generally having a particle size of less than about 1,000 μm, often less than about 750 μm. Often, topical compositions and/or skin cleansing compositions incorporate microbeads or particulates having a size of less than about 300 μm, and preferably, less than about 100 μm. Particulates, such as pumice can range from 35-1400 μm: topical compositions generally employ pumice having a particle size of about 100 μm. The particle size should be taken into consideration when employing a screen mask, as the particle size is generally less than about ⅓ of the opening in the screen. For larger particles it is more advantages to use stencil because there are screen limitations to consider. The microbeads can be a generally homogeneous material and can comprise pumice, polyethylene, glass, aluminum oxide, titanium dioxide, celluloses, such as Hydroxypropyl Methylcellulose (HPMC), or Vitamin E. Alternatively, the microbeads can be in the form of microencapsulated particles in which desirable material is encapsulated in a covering material to delay the release of the material to the environment. The microencapsulated particle may include adhesives and/or one or more benefit agents described in more detail below.

In a preferred embodiment, the film-forming composition, for example as shown in FIGS. 2 and 3, includes a benefit agent. The resulting multilayered film product 100 has a first surface 106 formed on a releasable surface of the substrate, and a second surface 108 opposite thereof. The first surface 106 is arranged and configured to deliver the benefit agent therethrough. For example, the first surface 106 may be protected by a release liner on a flexible substrate during manufacture and storage prior to use by a consumer. On the other hand, the second surface 108 is exposed to ambient conditions during the finishing of the raw shape. Thus, the first surface 106 may be tacky after removal from the substrate, and it may adhere to the skin of a consumer. The second surface 108 may "dry out" during transformation to the multilayered film product 100. Thus, the tacky first surface 106 can be ideal for delivery of a benefit agent to the skin of the consumer.

As used herein the specification and the claims, the term "benefit agent" and variants thereof relates to an element, an ion, a compound (e.g., a synthetic compound or a compound isolated from a natural source) or other chemical moiety in solid (e.g. particulate), liquid, or gaseous state and compound that has a cosmetic or therapeutic effect on the skin.

The compositions of the present invention may further include one or more benefit agents or pharmaceutically-acceptable salts and/or esters thereof, the benefit agents generally capable of interacting with the skin to provide a benefit thereto. As used herein, the term "benefit agent" includes any active ingredient that is to be delivered into and/or onto the skin at a desired location, such as a cosmetic or pharmaceutical.

The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

Examples of suitable benefit agents include those that provide benefits to the skin, such as, but not limited to, depigmentation agents; reflectants; film forming polymers; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; anti-infectives; anti-inflammatory agents; anticholinergics; vasoconstrictors; vasodilators; wound healing promoters; peptides, polypeptides and proteins; deodorants and antiperspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavenoids; sensates; antioxidants; hair lighteners, sunscreens; anti-edema agents, neo-collagen enhancers, film-forming polymers, chelating agents; anti-dandruff/sebhorreic dermatitis/psoriasis agents; keratolytics; and mixtures thereof.

In addition the benefit agent may also provide passive benefits to the skin. As such, the benefit agent may be formulated into a composition that include such ingredients as humectants or emollients, softeners or conditioners of the skin, make-up preparations, and mixtures thereof.

Examples of suitable anti-edema agents nonexclusively include bisabolol natural, synthetic bisabolol, corticosteroids, beta-glucans, and mixtures thereof.

Examples of suitable vasoconstrictors nonexclusively include horse chestnut extract, prickly ash, peroxides, tetrahydrozaline, and mixtures thereof.

Examples of suitable anti-inflammatory agents nonexclusively include benoxaprofen, *centella asiatica*, bisabolol, feverfew (whole), feverfew (parthenolide free), green tea extract, green tea concentrate, hydrogen peroxide, salicylates, oat oil, chamomile, and mixtures thereof.

Examples of neo-collagen enhancers nonexclusively include vitamin A and its derivatives (e.g. beta-carotene and retinoids such as retinoic acid, retinal, retinyl esters such as and retinyl palmitate, retinyl acetate and retinyl propionate); vitamin C and its derivatives such as ascorbic acid, ascorbyl phosphates, ascorbyl palmitate and ascorbyl glucoside; copper peptides; simple sugars such as lactose, mellibiose and fructose; and mixtures thereof.

Examples of enzymes include papain, bromelain, pepsin, and trypsin.

Examples of suitable skin firming agent nonexclusively include alkanolamines such as dimethylaminoethanol ("DMAE").

Examples of suitable antipruritics and skin protectants nonexclusively include oatmeal, beta-glucan, feverfew, soy products (by "soy product," it is meant a substance derived from soybeans, as described in United States Patent Application 2002-0160062), bicarbonate of soda, colloidal oatmeal, *Anagallis Arvensis, Oenothera Biennis, Verbena Officinalis*, and the like. As used herein, colloidal oatmeal means the powder resulting from the grinding and further processing of whole oat grain meeting United States Standards for Number 1 or Number 2 oats. The colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" available from the Beacon Corporation (Kenilworth, N.J.) and colloidal oatmeals available from Quaker (Chicago, Ill.).

Examples of suitable reflectants nonexclusively include mica, alumina, calcium silicate, glycol dioleate, glycol distearate, silica, sodium magnesium fluorosilicate, and mixtures thereof.

Examples of skin darkening agents nonexclusively include dihydroxy acetone, erythulose, melanin, and mixtures thereof.

Suitable film forming polymers include those that, upon drying, produce a substantially continuous coating or film on the skin or nails. Nonexclusive examples of suitable film forming polymers include acrylamidopropyl trimonium chloride/acrylamide copolymer; corn starch/acrylamide/sodium acrylate copolymer; polyquaternium-10, polyquaternium-47; polyvinylmethylether/maleic anhydride copolymer; styrene/acrylates copolymers; and mixtures thereof.

Commercially available humectants which are capable of providing moisturization and conditioning properties nonexclusively include: (i) water soluble liquid polyols selected from the group comprising glycerine, propylene glycol, hexylene glycol, butylene glycol, pentylene glycol, dipropylene glycol, and mixtures thereof; (ii) polyalkylene glycol of the formula HO—(R"O)b-H wherein R" is an alkylene group having from about 2 to about 4 carbon atoms and b is an integer of from about 1 to about 10, such as PEG 4; (iii) polyethylene glycol ether of methyl glucose of formula CH3-C6H10O5-(OCH2CH2)c-OH wherein c is an integer from about 5 to about 25; (iv) urea; (v) fructose; (vi) glucose; (vii) honey; (viii) lactic acid; (ix) maltose; (x) sodium glucuronate; and (xi) mixtures thereof, with glycerine being an exemplary humectant.

Suitable amino acids and derivatives include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, capryloyl collagen amino acids; capryloyl keratin amino acids; capryloyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultra-high-sulfur proteins, intermediate filament-associated proteins, high-tyrosine proteins, high-glycine tyrosine proteins, tricohyalin, and mixtures thereof.

Examples of suitable vitamins nonexclusively include various forms of vitamin B complex, including thiamine, nicotinic acid, biotin, pantothenic acid, choline, riboflavin, vitamin B3, vitamin B6, vitamin B12, pyridoxine, inositol, carnitine; vitamins A, C, D, E, K and their derivatives such as vitamin A palmitate and pro-vitamins, e.g. (i.e., panthenol (pro vitamin B5) and panthenol triacetate) and mixtures thereof.

Examples of suitable antimicrobial agents nonexclusively include bacitracin, erythromycin, neomycin, tetracycline, chlortetracycline, benzethonium chloride, phenol, benzyl peroxide, metal salts or ions such as silver and its salts and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of sunscreens, nonexclusively include benzophenones, bornelone, butyl paba, cinnamidopropyl trimethyl ammonium chloride, disodium distyrylbiphenyl disulfonate, PABA and its derivatives (such as octyl dimethyl PABA, butyl methoxydibenzoylmethane, isoamyl methoxycinnamate, methyl benzilidene camphor, octyl triazole, octyl methoxycinnamate, oxybenzone, octocrylene, octyl salicylate, homosalate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, MEXORYL S and SX, TINOSORB M and S, and mixtures thereof.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET, natural or synthetic pyrethroids, whereby the natural pyrethroids are contained in pyrethrum, the extract of the ground flowers of *Chrysanthemum cinerariaefolium* or *C coccineum*, and mixtures thereof. Within the structure of Formula III. are ethyl 3-(N-butylacetamido)propionate, wherein R7 is a CH3 group, R5 is an n-butyl group, R6 is H, K is COOR8 and R8 is ethyl, which is available commercially from Merck KGaA of Darmstadt, Germany under the name, "Insect Repellent 3535."

Examples of anti-fungals for foot preparations nonexclusively include tolnaftate and myconozole.

Examples of suitable depilating agents nonexclusively include calcium thioglycolate, magnesium thioglycolate, potassium thioglycolate, strontium thioglycolate, and mixtures thereof.

Examples of suitable analgesics such as external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone, *Fragaria Vesca*, *Matricaria Chamomilla*, and *Salvia Officinalis*.

Examples of suitable anaesthetic ingredients nonexclusively include the benzocaine, pramoxine hydrochloride, lidocaine, betacaine and mixtures thereof; antiseptics such as benzethonium chloride; astringents such as zinc oxide, bismuth subgallate, balsam Peru, and mixtures thereof; skin protectants such as zinc oxide, silicone oils, petrolatum, cod liver oil, vegetable oil, and mixtures thereof.

Examples of such suitable benefits agents effective in the treatment of dandruff, seborrheic dermatitis, and psoriasis, as well as the symptoms associated therewith nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan ("elubiol"), clotrimazole, itraconazole, miconazole, climbazole, tioconazole, sulconazole, butoconazole, fluconazole, miconazole nitrate and any possible stereo isomers and derivatives thereof; piroctone olamine (Octopirox); ciclopirox olamine; anti-psoriasis agents such as vitamin D analogs, e.g. calcipotriol, calcitriol, and tacaleitrol; vitamin A analogs such as esters of vitamin A, e.g. vitamin A palmitate and vitamin A acetate, retinyl propionate, retinaldehyde, retinol, and retinoic acid; corticosteroids such as hydrocortisone, clobetasone, butyrate, clobetasol propionate menthol, pramoxine hydrochloride, and mixtures thereof.

Examples of benefit agents suitable for treating hair loss include, but are not limited to potassium channel openers or peripheral vasodilators such as minoxidil, diazoxide, and compounds such as N*-cyano-N-(tert-pentyl)-N'-3-pyridinyl-guanidine ("P-1075"), saw palmetto extract, vitamins, such as vitamin E and vitamin C, and derivatives thereof such as vitamin E acetate and vitamin C palmitate; hormones, such as erythropoietin, prostaglandins, such as prostaglandin EI and prostaglandin F2-alpha; fatty acids, such as oleic acid; diruretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as retinal and tretinoin; cytokines, such as IL-6, IL-1 alpha, and IL-1 beta; cell adhesion molecules such as CAM; glucorcorticoids such as betametasone; botanical extracts such as aloe, clove, ginseng, rehmannia, swertia, sweet orange, zanthoxylum, *Serenoa repens* (saw palmetto), *Hypoxis rooperi*, stinging nettle, pumpkin seeds, and rye pollen; other botanical extracts including sandlewood, red beet root, *chrysanthemum*, rosemary, burdock root and other hair growth promoter activators; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem, hexachlorobenzene; hydantoin; nifedipine; penicillamine; phenothaiazines; pinacidil; psoralens, verapamils zidovudine; alpha-glucosylated rutin having at least one of the following rutins: quercetin, isoquercitrin, hespeddin, naringin, and methyl-hesperidin, and flavonoids and transglycosidated derivatives thereof; and mixtures thereof.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin; gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof.

Examples of suitable anti-aging agents include, but are not limited to inorganic sunscreens such as titanium dioxide and zinc oxide; organic sunscreens such as octyl-methoxy cinnamates and derivatives thereof; retinoids; copper containing peptides; vitamins such as vitamin E, vitamin A, vitamin C, vitamin B, and derivatives thereof such as vitamin E acetate, vitamin C palmitate, and the like; anti-oxidants including beta carotene, alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; polyphenolics; botanical extracts such as green tea, soy products, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the antiinflammatory agents such as ibuprofen, naproxen, hetprofen; botanical extracts such as alnus, arnica, *artemisia capillaris, asiasarum* root, birrh, calendula, chamomile, cnidium, comfrey, fennel, *galla rhois*, hawthorn, houttuynia, hypericum, jujube, kiwi, licorice, magnolia, olive, peppermint, philodendron, salvia, sasa albo-marginate; imidazoles such as ketoconazole and elubiol.

Examples of suitable depigmentation agents include, but are not limited to soy products, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinoids, Kojic acid, soy products, and hydroquinone being particularly suitable examples.

Examples of suitable anti-hemorrhoidal products include, but are not limited to anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Examples of vasodilators include, but are not limited to minoxidil, diazoxide, and compounds such as N*-cyano-N-(tert-pentyl)-N'-3-pyridinyl-guanidine ("P-1075").

Examples of suitable shine-control agents include, but are not limited to hydrated silica, kaolin, and bentonite. Examples of suitable anti-histamines include, but are not limited to diphenhydramine HCl. Examples of suitable antiinfectives include, but are not limited to benzalkonium chloride, hexamidine, and hydrogen peroxide. Examples of suitable wound healing promoters include, but are not limited to chitosan and its derivatives. Examples of suitable poison ivy and poison oak products include, but are not limited to bentonite, hydrocortisone, menthol, and lidocaine. Examples of burn products include, but are not limited to benzocaine and lidocaine. Examples of suitable anti-diaper rash products include but are not limited to zinc oxide and petrolatum. Examples of suitable prickly heat products include, but are not limited to zinc oxide. Examples of suitable sensates include, but are not limited to menthol, fragrances, and capsaicin.

Benefit agents that may be particularly suitable for use with the multilayered film product 100 include, DMAE, soy products, colloidal oatmeal, sulfonated shale oil, olive leaf, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, copper containing compounds such as copper containing peptides and copper salts, hydrolyzed silk proteins, octyl methoxycinnamate, oxybenzone, avobenzone, minoxidil, saw palmetto extract, titanium dioxide, zinc dioxide, retinol, erthromycin, tretinoin, and mixtures thereof.

Benefit agents that may be of particularly suitable for use the multilayered film product 100 include neo-collagen promoters (e.g. retinoids such as retinal and copper-containing peptides), skin firming agents (e.g. DMAE), and depigmenting agents (e.g. soy).

The amount of the benefit agent that may be used may vary depending upon, for example, the ability of the benefit agent to penetrate through the skin or nail, the specific benefit agent chosen, the particular benefit desired, the sensitivity of the user to the benefit agent, the health condition, age, and skin and/or nail condition of the user, and the like. In sum, the benefit agent is used in a "safe and effective amount," which is an amount that is high enough to deliver a desired skin or nail benefit or to modify a certain condition to be treated, but is low enough to avoid serious side effects, at a reasonable risk to benefit ratio within the scope of sound medical judgment.

The benefit agent may be formulated, mixed, or compounded with other ingredients into a composition (e.g. liquid, emulsion, cream, and the like) wherein the other ingredients do not detract from the functionality of the benefit agent. A delivery agent that enhances the absorption of the one or more benefit agents into the skin may be formulated with the benefit agent to fulfill this function. Suitable delivery agents include, for example, sulfoxides, alcohols such as ethanol; fatty acids such as, for example, linoleic acid or oleic acid, fatty esters such as, for example, may be produced from reacting a C3-C10 carboxylic acid with a C10-C20 fatty alcohol; a polyol, an alkane, an amine, an amide, a turpene, a surfactant, a cyclodextrin or combinations thereof among other agents known to the art to be suitable for enhancing the penetration of various benefit agents through the stratum corneum into deeper layers of the skin.

The concentration of the benefit agent within the composition is variable. Unless otherwise expressed herein, typically the benefit agent is present in the composition in an amount, based upon the total weight of the composition/system, from about 0.01 percent to about 20 percent, such as from about 0.01 percent to about 5 percent (e.g., from about 0.01 percent to about 1 percent).

This composition that includes the benefit agent may also serve as a coupling composition as described previously and may include ingredients that enable the composition to possess one of these functions.

In addition to, or in place of one or more of the components described above, fragrances, flavors, sweeteners, coloring agents, pigments, dyes and the like may be added to the film-forming composition of the present invention.

EXAMPLES

The present invention will be further understood by reference to the following specific Examples that are illustrative of the composition, form and method of producing the device of the present invention. It is to be understood that many variations of composition, form and method of producing the device would be apparent to those skilled in the art. The following Examples, wherein parts and percentages are by weight unless otherwise indicated, are only illustrative.

Film-forming compositions were prepared with the %-solids and viscosity values in the Table 1, below:

TABLE 1

| For-mula | Ingredients | Weight (g) | %-solids | Viscosity (cP)[1] |
|---|---|---|---|---|
| 1 | FD&C Red 40 | 0.02 | 24 | 6650 |
|  | Keltrol CG-T, Xanthan Gum | 0.04 |  |  |
|  | TIC Pretested Locust Bean Gum POR/A Powder | 0.07 |  |  |
|  | Copper Gluconate Powder | 0.36 |  |  |
|  | Acesulfame K, Particle Size A | 0.51 |  |  |
|  | Thymol | 0.15 |  |  |
|  | Methyl Salicylate | 0.22 |  |  |
|  | Eucalyptol USP | 0.25 |  |  |
|  | Polysorbate 80 N.F. | 0.35 |  |  |
|  | Atmos 300K | 0.35 |  |  |
|  | Ticaloid 750 Carrageenan | 0.35 |  |  |
|  | Pullulan, Cosmetic Grade | 16.48 |  |  |
|  | Sucralose, Micronized NF | 1.01 |  |  |
|  | Cinnamon Flavor SN313574 | 1.25 |  |  |
|  | Menthol USP TA | 2.39 |  |  |
|  | Water, Purified | 76.20 |  |  |
| 2 | FD&C Red 40 | 0.02 | 30 | 17950 |
|  | Keltrol CG-T, Xanthan Gum | 0.04 |  |  |
|  | TIC Pretested Locust Bean Gum POR/A Powder | 0.07 |  |  |
|  | Copper Gluconate Powder | 0.36 |  |  |
|  | Acesulfame K, Particle Size A | 0.51 |  |  |
|  | Thymol | 0.15 |  |  |
|  | Methyl Salicylate | 0.22 |  |  |
|  | Eucalyptol USP | 0.25 |  |  |
|  | Polysorbate 80 N.F. | 0.35 |  |  |
|  | Atmos 300K | 0.35 |  |  |
|  | Ticaloid 750 Carrageenan | 0.35 |  |  |
|  | Pullulan, Cosmetic Grade | 16.48 |  |  |
|  | Sucralose, Micronized NF | 1.01 |  |  |
|  | Cinnamon Flavor SN313574 | 1.25 |  |  |
|  | Menthol USP TA | 2.39 |  |  |
|  | Water, Purified | 55.00 |  |  |
| 3 | FD&C Red 40 | 0.0200 | 38 | 90800 |
|  | Keltrol CG-T, Xanthan Gum | 0.0400 |  |  |
|  | TIC Pretested Locust Bean Gum POR/A Powder | 0.0700 |  |  |
|  | Copper Gluconate Powder | 0.36 |  |  |
|  | Acesulfame K, Particle Size A | 0.51 |  |  |
|  | Thymol | 0.15 |  |  |
|  | Methyl Salicylate | 0.22 |  |  |
|  | Eucalyptol USP | 0.25 |  |  |
|  | Polysorbate 80 N.F. | 0.35 |  |  |
|  | Atmos 300K | 0.35 |  |  |
|  | Ticaloid 750 Carrageenan | 0.35 |  |  |
|  | Pullulan, Cosmetic Grade | 16.48 |  |  |
|  | Sucralose, Micronized NF | 1.01 |  |  |
|  | Cinnamon Flavor SN313574 | 1.25 |  |  |
|  | Menthol USP TA | 2.39 |  |  |
|  | Water, Purified | 55.00 |  |  |
| 4 | SELVOL 805 | 22.973 | 25 | 1350 |
|  | Polysorbate 80 | 1.750 |  |  |
|  | Dow Corning 2501 Cosmetic Wax | 0.800 |  |  |
|  | Kester Wax K-24 | 0.800 |  |  |
|  | Glycerin 99.7%, USP | 2.125 |  |  |
|  | Water, purified | 85.000 |  |  |
| 5 | Selvol 805 | 22.9730 | 38 | 57600 |
|  | Polysorbate 80 | 1.7500 |  |  |
|  | Dow Corning 2501 Cosmetic Wax | 0.8000 |  |  |
|  | Kester Wax K-24 | 0.8000 |  |  |
|  | Glycerin 99.7%, USP | 2.1250 |  |  |
|  | Water, Purified | 45.0000 |  |  |
| 6 | RED ink Speedball[2] #4601 | — |  | 17450 |
| 7 | BLACK ink Speedball[2] #4600 | — |  | 20050 |

[1]Viscosity in centipoise (cP) was measured with a calibrated Brookfield Viscometer. The test method was standardized to:
Temperature: 70° F. (21° C.)
Spindle # RV S06
Motor speed 20 rpm.
[2]The screen printing ink used for testing is manufactured by Speedball Art Products, LLC, 2301 Speedball Road, Statesville, NC 28677 USA, % solids was not recorded.

Examples 1-18: Stencil Printing

Stencil material: plastic shim stock, shape cut-out via laser, substrate poly coated paper (ULINE® Freezer Paper #S7045. 40 lb. virgin paper bleached white and coated with 5 lb. polyethylene on one side, available from Uline, Pleasant Prairie, Wis., USA).

Stenciling done on the flat, by hand, over smooth flat glass backup, with 4" wide stiff scraper blade (similar putty knife and/or dry wall tool can substitute for the blade)

Five of the film-forming compositions of Table 1 were deposited using a blade and a stencil with the thickness in Table 2 below. The resulting integral film products were dried, removed from the substrate, and measured.

TABLE 2

| Example # | Formula | Stencil Thickness (inch) | Stencil Thickness (mm) | Avg. Dry Thickness[3] (in) |
|---|---|---|---|---|
| 1 | 1 | 0.005 | 0.13 | 0.002 |
| 2 | 1 | 0.007 | 0.18 | 0.002 |
| 3 | 1 | 0.010 | 0.25 | 0.003 |
| 4 | 1 | 0.020 | 0.51 | 0.005 |
| 5 | 1 | 0.030 | 0.76 | 0.007 |
| 6 | 1 | 0.040 | 1.02 | 0.011 |
| 7 | 2 | 0.005 | 0.13 | 0.003 |
| 8 | 2 | 0.007 | 0.18 | 0.003 |
| 9 | 2 | 0.010 | 0.25 | 0.004 |
| 10 | 2 | 0.020 | 0.51 | 0.007 |
| 11 | 2 | 0.030 | 0.76 | 0.011 |
| 12 | 2 | 0.040 | 1.02 | 0.014 |
| 13 | 3 | 0.005 | 0.13 | 0.004 |
| 14 | 3 | 0.007 | 0.18 | 0.005 |
| 15 | 3 | 0.010 | 0.25 | 0.006 |
| 16 | 3 | 0.020 | 0.51 | 0.009 |
| 17 | 3 | 0.030 | 0.76 | 0.015 |
| 18 | 3 | 0.040 | 1.02 | 0.019 |

[3]Average of the maximum and minimum values for two individual dried film products.

Figure 18:
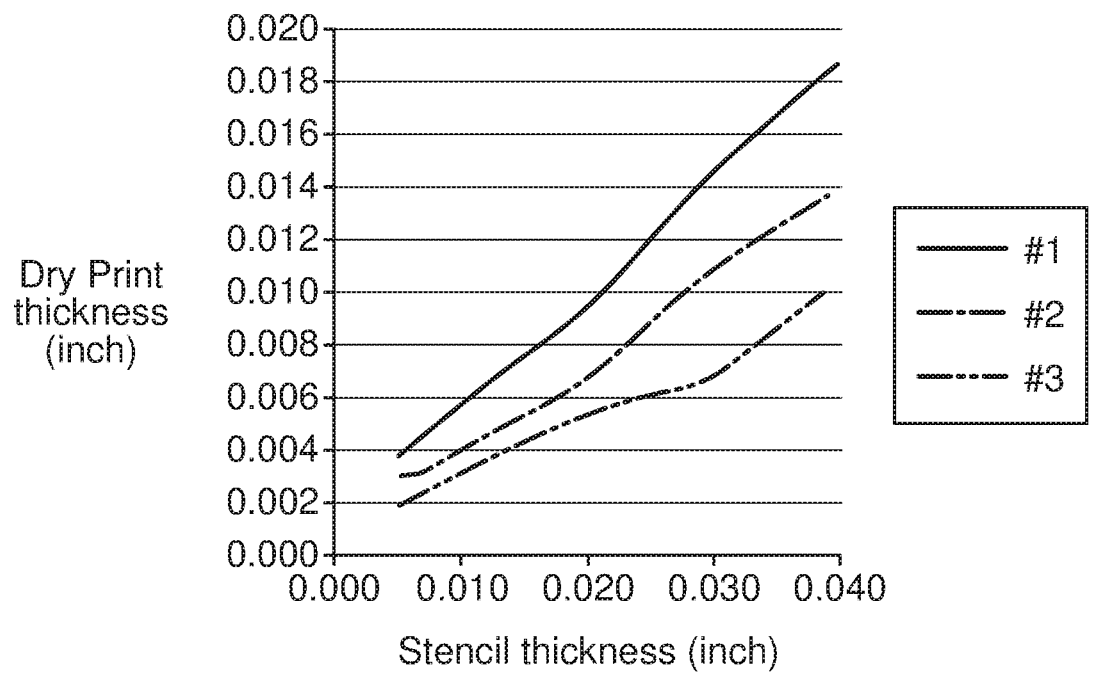
FIG. 18 is a graph of stencil mask to finished product thickness.

These results were plotted in a graph (FIG. 18) showing the linear relationship between the thickness of the stencil thickness and the solidified film product for Formulas 1-3.

Examples 19-34: Screen Printing

A rotary module screen printing apparatus (per FIG. 3) with a drum diameter of 5 inches was used. The outer surface of the drum was defined by a 0.003 inch nickel screen (40×40 mesh (openings/inch)) and a mask having the thickness identified in Table 3 (from 0.010 to 0.030 inches) was formed on the inner surface of the mesh. The film-forming compositions were deposed on a substrate as in Examples 1-18 (ULINE® Freezer Paper #S7045). The results are shown in Table 3.

TABLE 3

| Example # | Formula | Mask Thickness (inch) | Mask Thickness (mm) | Avg. Dry Thickness[4] (in) | Observations |
|---|---|---|---|---|---|
| 19 | 1 | 0.01 | 0.25 | 0.0023 | Some formula sticks to screen; bubbles in printed pattern dissipate over 2-3 minutes |
| 20 | 1 | 0.01 | 0.25 | 0.0020 |  |
| 21 | 2 | 0.01 | 0.25 | 0.0034 |  |
| 22 | 2 | 0.01 | 0.25 | 0.0030 | Some formula sticks to screen |

TABLE 3-continued

| Example # | Formula | Mask Thickness (inch) | Mask Thickness (mm) | Avg. Dry Thickness[4] (in) | Observations |
|---|---|---|---|---|---|
| 23 | 3 | 0.01 | 0.25 | 0.0042 | (less than Ex. 31); smaller bubbles than Ex. 31. Transferred from screen well; rough edges; most bubbles disappear during drying |
| 24 | 3 | 0.02 | 0.51 | 0.0090 | Required 2 squeegee wipes to fill and transfer; not all patterns transferred from screen |
| 25 | 4 | 0.02 | 0.51 | 0.0044 | Very thin; formulation runs; wide variations in finished product thickness |
| 26 | 5 | 0.02 | 0.51 | 0.0158 | Formulation is sticky and stringy; only partial release from screen |
| 27 | 1 | 0.02 | 0.51 | 0.0036 | Numerous bubbles that disappear within 3 minutes. |
| 28 | 2 | 0.02 | 0.51 | 0.0065 | Required 2 squeegee wipes to fill and transfer; not all patterns transferred from screen |
| 29 | 6 | 0.02 | 0.51 | 0.0059 | Numerous bubbles |
| 30 | 7 | 0.02 | 0.51 | 0.0058 | No bubbles, but ribbing effect; texture remains upon drying |
| 31 | 6 | 0.01 | 0.25 | 0.0025 | Numerous bubbles |
| 32 | 7 | 0.01 | 0.25 | 0.0025 | No bubbles, but ribbing effect; texture remains upon drying |
| 33 | 1 | 0.03 | 0.76 | 0.0053 | Very thin; formulation runs and sticks to screen |
| 34 | 2 | 0.03 | 0.76 | 0.0091 | Requires multiple squeegee passes to fill and transfer formulation |

[4]Average of the maximum and minimum values for six two individual dried films products.

Figure 19:
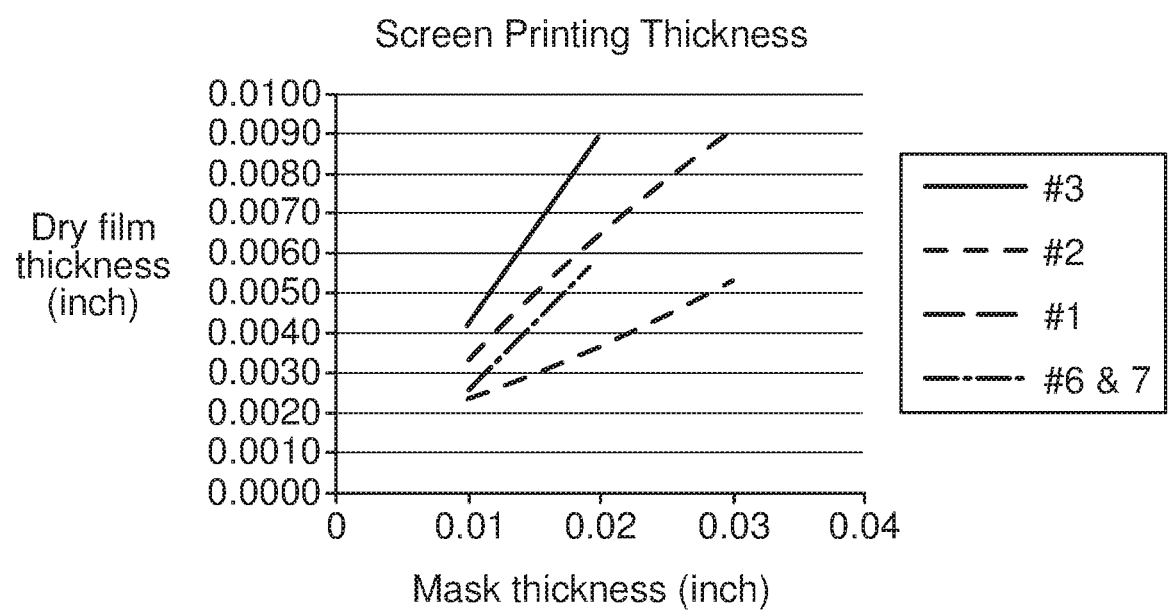
FIG. 19 is a graph of screen mask to finished product thickness.

These results were plotted in a graph (FIG. 19) showing the linear relationship between the thickness of the stencil thickness and the integral film product. The data includes Formulas 1-3, separately, and Formulas 6 and 7 combined, as the % solids was believed to be substantially the same and the resulting dry film thickness was substantially the same for a given mask thickness.

Examples 35-39: Screen Printing of Second Layer

Figure 20:
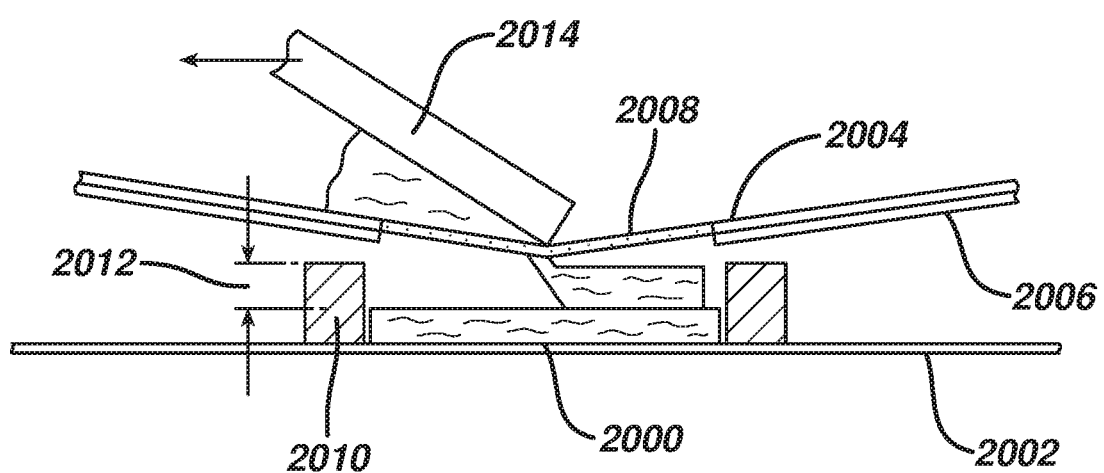
FIG. 20 is a schematic side view of a flatbed screen printer device in use according to one embodiment of the present invention, used to make examples described herein.

A flatbed screen printer (Systematic Automation Inc, Bloomfield Connecticut Model F1-12), shown in part in FIG. 20 was used in Examples 35-39. FIG. 20 shows a stencil-printed first layer 2000 that was deposited on the polycoated paper 2002 of Examples 1-18 (ULINE® Freezer Paper #S7045). The first layer 2000 was a 1-inch (25.4 mm) diameter circle formed with a stencil mask of 0.005 inch (0.013 mm) thickness. A woven wire screen 2004 (60×60 mesh formed of 304 stainless steel wire having a 0.0075 inch (0.2 mm) diameter) with a mask 2006 (0.002 inch (0.05 mm) polyester shim stock epoxied to the screen) having a circular opening 2008 (0.875 inch (22 mm) diameter) was placed over the first layer 2000 and separated from the polycoated paper 2003 by means of a spacer 2010 placed around the first layer 2000. The spacer 2010 defined a gap 2012 between the top of the first layer 2000 and the screen 2004. This gap 2012 defines the thickness of the second layer. With the screen 2004 in place over the first layer 2000, a squeegee 2014 was drawn in the direction of arrow 2016 to force the film-forming composition 2018 through the screen opening 2008 to form the second layer 2020 on top of the first layer 2000. The screen 2004 was then raised and removed, and the samples were dried in an oven and the thickness was measured. The results are shown in Table 4, below using Formulas 6 and 7 from Table 1, however, the viscosity of these inks was modified to provide comparisons of viscosity on top and bottom layers. The viscosity of each Formula was reported in the table.

TABLE 4

| Example | Bottom Formula | Viscosity cP | Stencil Thickness (inch) | Top Formula | Viscosity cP | Spacer Thickness (inch) | GAP (inch) |
|---|---|---|---|---|---|---|---|
| 35 | 7 | 15,800 | 0.005 | 6 | 14,800 | 0.01 | 0.005 |
| 36 | 6 | 14,800 | 0.005 | 7 | 15,800 | 0.01 | 0.005 |
| 37 | 7 | 15,800 | 0.005 | 6 | 10,800 | 0.01 | 0.005 |
| 38 | 7 | 15,800 | 0.005 | 6 | 7,400 | 0.01 | 0.005 |
| 39 | 7 | 10,500 | 0.005 | 6 | 14,800 | 0.01 | 0.005 |

The thickness of Example 35 was measured, and the dry thickness of the top and bottom layers was recorded as 0.0015 inch.

Example 35 resulted in a relatively uniform top layer.

Example 36 showed that the bottom layer, having a lower viscosity, was very flat, and the top layer was thicker.

Example 37 had a more pronounced viscosity differential, and the screen contacted the bottom layer during deposition, texturing the bottom layer.

Example 38 had a significantly more pronounced viscosity differential, with the top layer having a viscosity about 50% of the bottom layer. Again the screen contacted the bottom layer during deposition, and the top layer ink had significant bubbles formed therein that were maintained in the dried product.

Example 39, with a significantly higher viscosity formulation in the top layer did not release from the screen to the bottom layer very well. In addition, the noticeable amounts of the bottom layer adhered to the screen/top layer formulation after removal of the screen during printing.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An integral multilayered shaped film product having a perimeter and comprising a first layer comprising a first film material and having side edges and a second layer comprising a second film material disposed on the first layer having side edges spaced inward from the side edges of the first layer, wherein at least one of the first and second layers comprises a benefit agent and wherein a plurality of integral multilayered shaped product arrayed on a surface, each integral multilayered shaped product having at least a portion of its perimeter in contact with adjoining integral multilayered shaped products, must leave gaps between at least a portion of the respective perimeters of such adjoining integral multilayered shaped products.

2. The integral multilayered shaped film product of claim 1 wherein the second layer comprises a plurality of spaced apart regions.

3. The integral multilayered shaped film product of claim 2 wherein the plurality of spaced apart regions comprise additional film materials.

4. An integral multilayered shaped film product having a perimeter and comprising a first surface having a first film material substantially surrounded by a second film material and a second surface formed by the second film material, wherein at least one of the first and second layers comprises a benefit agent and wherein a plurality of integral multilayered shaped product arrayed on a surface, each integral multilayered shaped product having at least a portion of its perimeter in contact with adjoining integral multilayered shaped products, must leave gaps between at least a portion of the respective perimeters of such adjoining integral multilayered shaped products.

5. The integral multilayered shaped film product of claim 4 further comprising additional film materials disposed in the first surface, substantially surrounded by the first film material.

6. An integral multilayered shaped film product having a perimeter and comprising a first continuous layer having side edges and a second layer having side edges disposed thereon, the second layer having a void spaced inward from its side edges, wherein the at least one of the first and second layers comprises a benefit agent and wherein a plurality of integral multilayered shaped product arrayed on a surface, each integral multilayered shaped product having at least a portion of its perimeter in contact with adjoining integral multilayered shaped products, must leave gaps between at least a portion of the respective perimeters of such adjoining integral multilayered shaped products.

7. The integral multilayered shaped film product of claim 6, wherein the side edges of the second layer are spaced inward from the side edges of the first continuous layer.

* * * * *